(12) United States Patent
Maezawa

(10) Patent No.: US 12,011,068 B2
(45) Date of Patent: *Jun. 18, 2024

(54) SIZE MEASUREMENT SYSTEM

(71) Applicant: ZOZO, Inc., Chiba (JP)

(72) Inventor: Yusaku Maezawa, Chiba (JP)

(73) Assignee: ZOZO, Inc., Chiba (JP)

( * ) Notice: Subject to any disclaimer, the term of this patent is extended or adjusted under 35 U.S.C. 154(b) by 569 days.

This patent is subject to a terminal disclaimer.

(21) Appl. No.: 17/278,115

(22) PCT Filed: Sep. 17, 2019

(86) PCT No.: PCT/JP2019/036402
§ 371 (c)(1),
(2) Date: Mar. 19, 2021

(87) PCT Pub. No.: WO2020/059716
PCT Pub. Date: Mar. 26, 2020

(65) Prior Publication Data
US 2021/0345733 A1 Nov. 11, 2021

(30) Foreign Application Priority Data

Sep. 21, 2018 (JP) ................................ 2018-178086
Mar. 29, 2019 (WO) .................. PCT/JP2019/014227

(51) Int. Cl.
*G06T 17/00* (2006.01)
*A43D 1/02* (2006.01)
(Continued)

(52) U.S. Cl.
CPC ................ *A43D 1/02* (2013.01); *G06T 17/00* (2013.01); *G06T 19/20* (2013.01); *G06T 7/50* (2017.01)

(58) Field of Classification Search
CPC .......... A43D 1/02; A43D 1/025; G06T 17/00; G06T 19/20; G06T 7/50;
(Continued)

(56) References Cited

U.S. PATENT DOCUMENTS

| 6,549,639 | B1 | 4/2003 | Genest |
| 6,621,921 | B1 | 9/2003 | Matsugu et al. |

(Continued)

FOREIGN PATENT DOCUMENTS

| EP | 2747593 A1 | 7/2014 |
| JP | 9-170914 | 6/1997 |

(Continued)

OTHER PUBLICATIONS

Current claims of co-pending related U.S. Appl. No. 17/043,230, filed Sep. 29, 2020.

(Continued)

*Primary Examiner* — Said M Elnoubi
(74) *Attorney, Agent, or Firm* — Renner, Otto, Boisselle & Sklar, LLP

(57) ABSTRACT

Provided is a size measurement system for measuring the size of a user's foot, said system characterized by comprising: a size measurement instrument which is formed from a stand for the user to place the foot thereon, and a plurality of markers which are positioned in the periphery of the stand; and a measurement terminal which captures an image of a state in which the user has placed the foot on the stand in the size measurement instrument such that the plurality of markers can be recognized from a plurality of directions, and which computes size data for the foot from contour information for the foot obtained through the image capture from each of the directions

12 Claims, 18 Drawing Sheets

(51) Int. Cl.
*G06T 19/20* (2011.01)
*G06T 7/50* (2017.01)

(58) Field of Classification Search
CPC . G06T 2207/10004; G06T 2207/10016; G06T 2207/30196; G06T 7/564; G06T 2207/30208; G06T 7/62; A61B 5/706; A61B 5/743; A61B 5/0077; A61B 5/1074; A61B 5/1079
See application file for complete search history.

(56) References Cited

U.S. PATENT DOCUMENTS

| | | | |
|---|---|---|---|
| 6,724,930 B1 * | 4/2004 | Kosaka | G06V 10/757 382/154 |
| 2004/0227752 A1 | 11/2004 | McCartha et al. | |
| 2007/0206832 A1 | 9/2007 | Gordon et al. | |
| 2012/0095589 A1 | 4/2012 | Vapnik | |
| 2013/0293686 A1 | 11/2013 | Blow et al. | |
| 2014/0343628 A1 | 11/2014 | Kaula et al. | |
| 2016/0071318 A1 | 3/2016 | Lee et al. | |
| 2016/0071322 A1 | 3/2016 | Nishiyama et al. | |
| 2016/0163104 A1 | 6/2016 | Hou | |
| 2018/0033202 A1 * | 2/2018 | Lam | G06V 40/10 |
| 2020/0367590 A1 | 11/2020 | Istook et al. | |

FOREIGN PATENT DOCUMENTS

| | | | | |
|---|---|---|---|---|
| JP | 2000227309 | A | 8/2000 | |
| JP | 2001204511 | A | 7/2001 | |
| JP | 2002163679 | A | 6/2002 | |
| JP | 2002213923 | A | 7/2002 | |
| JP | 2005256232 | A | 9/2005 | |
| JP | 2005258891 | A | 9/2005 | |
| JP | 200753818 | A | 3/2007 | |
| JP | 2007267996 | A | 10/2007 | |
| JP | 201654450 | A | 4/2016 | |
| JP | 2018019843 | A | 2/2018 | |
| WO | 2013026798 | A1 | 2/2013 | |
| WO | WO-2013026798 | A1 * | 2/2013 | ............. A43D 1/025 |
| WO | 2013026798 | A1 | 2/2018 | |

OTHER PUBLICATIONS

Second Office Action for corresponding Canadian Application No. 3,113,602 dated Jan. 30, 2023.
New Zealand second Patent Examination Report corresponding to New Zealand Application No. 769366 dated Oct. 6, 2022.
Extended European Search Report corresponding to European Application No. EP19861345.7 dated May 10, 2022.
Japanese Office Action corresponding to Japanese Application No. 2020-548520 mailed May 6, 2022 and its English Translation.
New Zealand first Patent Examination Report corresponding to New Zealand Application No. 769366 dated May 10, 2022.
Extended European Search Report for related European Application No. 19776139.8 dated Dec. 1, 2021.
First Examination Report for related Indian Application No. 202047041455 dated Dec. 7, 2021 and its English translation.
First Examination Report for related Indian Application No. 202147018290 dated Feb. 8, 2022 and its English translation.
Loper Matthew et al: "MoSh: motion and shape capture from sparse markers", ACM Transactions on Graphics, vol. 33, No. 6, Nov. 19, 2014, pp. 1-13, XP055862859.
Office Action for related U.S. Appl. No. 17/043,230 dated Jan. 31, 2022.
First Office Action for corresponding Japanese Application No. 2021-186434 mailed Dec. 1, 2022 and its English Machine Translation.
Final Office Action for related Japanese Application No. 2021-186434 dated Jul. 14, 2023 and its English Machine translation.
Denial of Entry of Amendment for related Japanese Application No. 2021-186434 dated Jul. 14, 2023 and its English Machine translation.
First Office Action for related Israel Application No. 277581 dated Aug. 2, 2023 and its English language summary.
International Search Report for related International Application No. PCT/JP2019/036402 mailed Nov. 19, 2019 and its English translation.
International Search Report for priority International Application No. PCt/JP2019/014227 mailed May 14, 2019 and its English translation.
Second Office Action for corresponding Japanese Application No. 2021-186434 dated Apr. 10, 2023 and its English translation.
Hashimoto et al., Robot Vision Sensor, Mitsubishi Electric Engineering Co., Ltd., vol. 73, No. 8, pp. 60 (602)-63 (1999) and its partial English translation.
First Office Action for related Chinese Application No. 201980071239.9 dated Sep. 15, 2023 and its English translation.

* cited by examiner

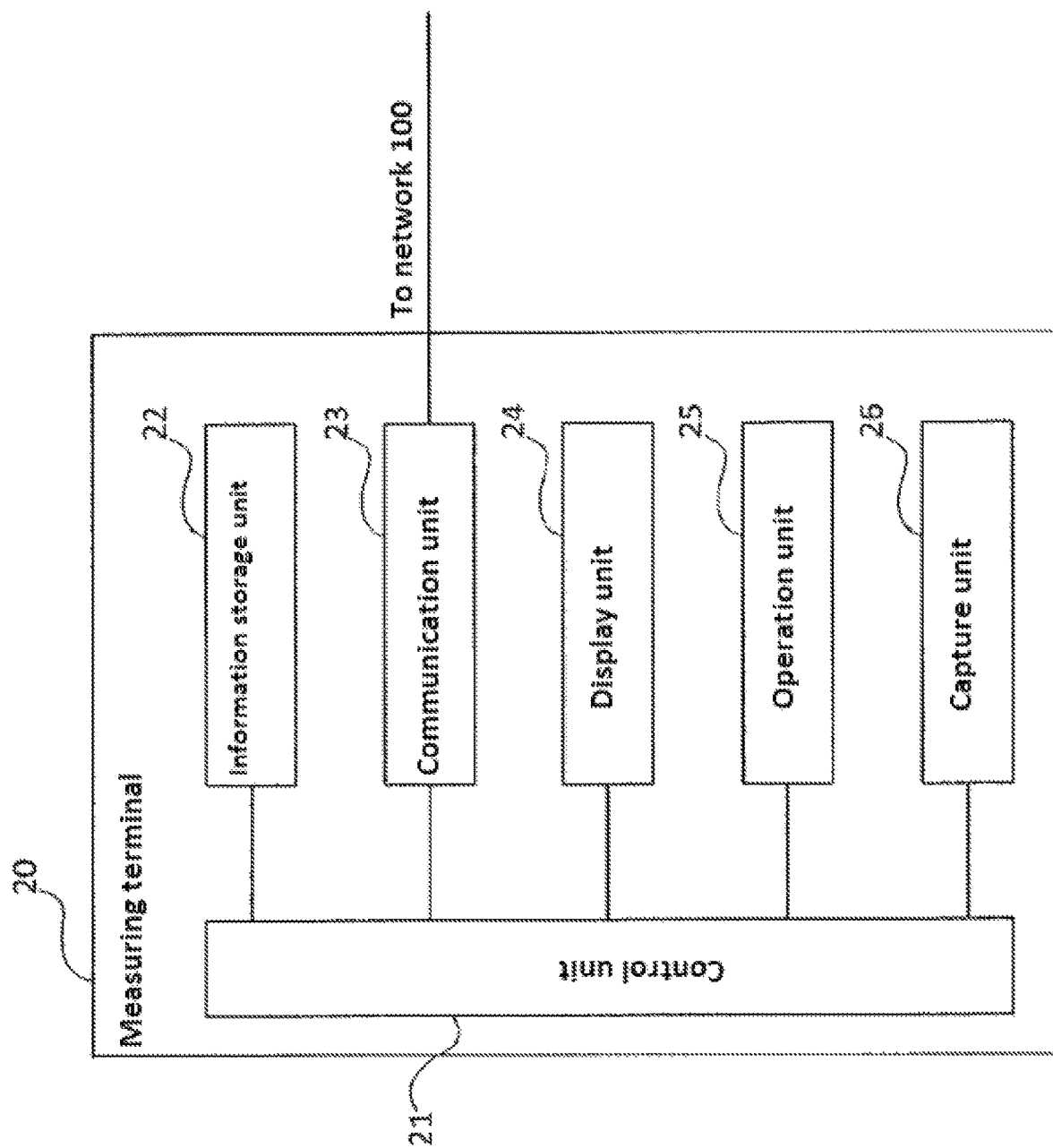

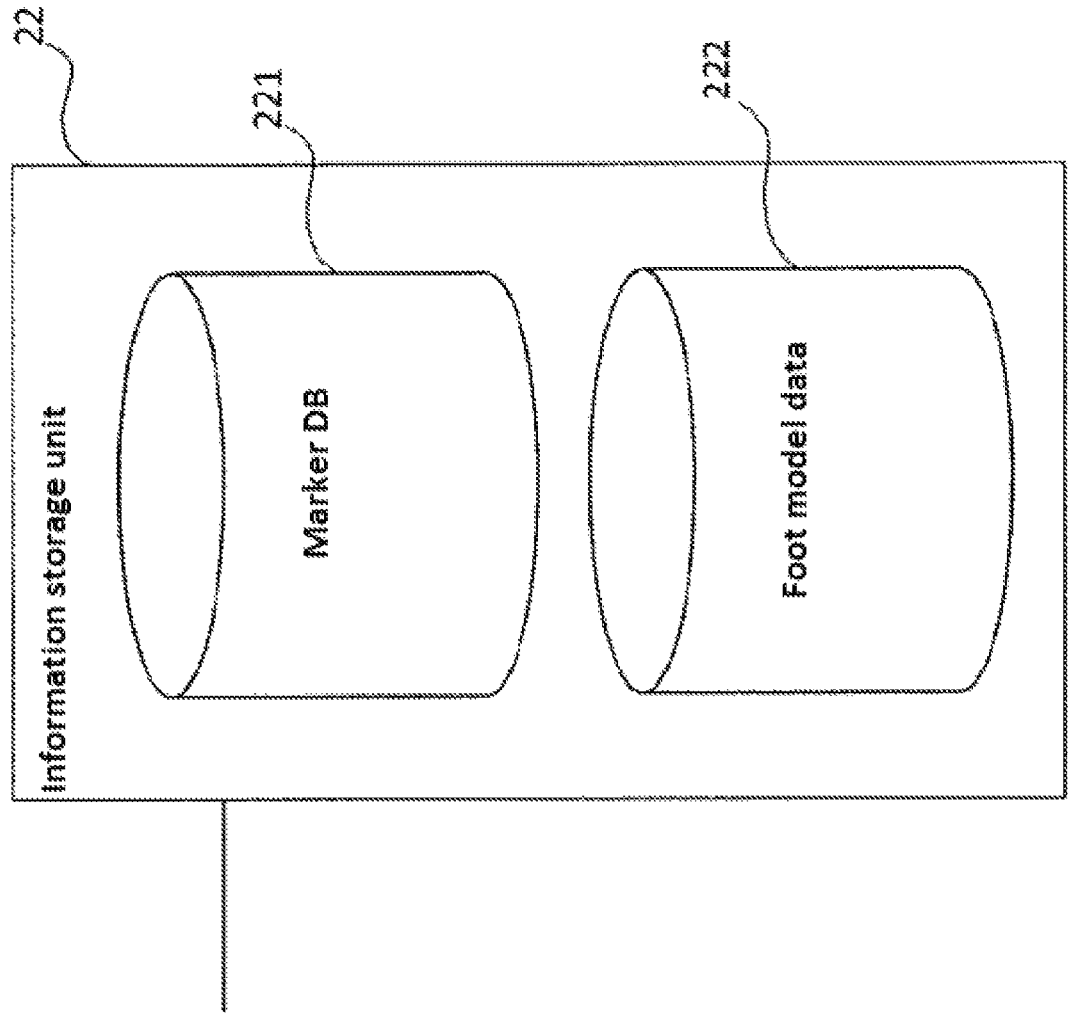

FIG.6

| Marker ID | Shape | Size | Design/pattern | Color tone | Material | Key marker |
|---|---|---|---|---|---|---|
| 0001 | ... | ... | ... | ... | ... | |
| 0002 | ... | ... | ... | ... | ... | ○ |
| 0003 | ... | ... | ... | ... | ... | |
| 0004 | ... | ... | ... | ... | ... | |
| 0005 | ... | ... | ... | ... | ... | ○ |
| 0006 | ... | ... | ... | ... | ... | |
| 0007 | ... | ... | ... | ... | ... | |
| 0008 | ... | ... | ... | ... | ... | ○ |
| 0009 | ... | ... | ... | ... | ... | |
| 0010 | ... | ... | ... | ... | ... | |
| ... | ... | ... | ... | ... | ... | |

FIG.11

| Product ID | Brand | Product category | Size information | Color | Price | Number in stock |
|---|---|---|---|---|---|---|
| 0001 | AAA | Leather shoes | ... | Black | 15,000 | 10 |
| 0002 | AAA | Leather shoes | ... | Black | 20,000 | 30 |
| 0003 | AAA | Sneakers | ... | White | 12,000 | 25 |
| 0004 | AAA | Sneakers | ... | Gray | 8,000 | 40 |
| 0005 | BBB | Sandals | ... | Red | 10,000 | 100 |
| 0006 | BBB | Sneakers | ... | Blue | 7,500 | 60 |
| 0007 | BBB | Pumps | ... | Black | 5,000 | 120 |
| 0008 | CCC | Pumps | ... | Red | 5,000 | 110 |
| 0009 | CCC | Pumps | ... | Brown | 5,000 | 114 |
| 0010 | CCC | Pumps | ... | Brown | 5,000 | 32 |
| ... | ... | ... | ... | ... | ... | ... |

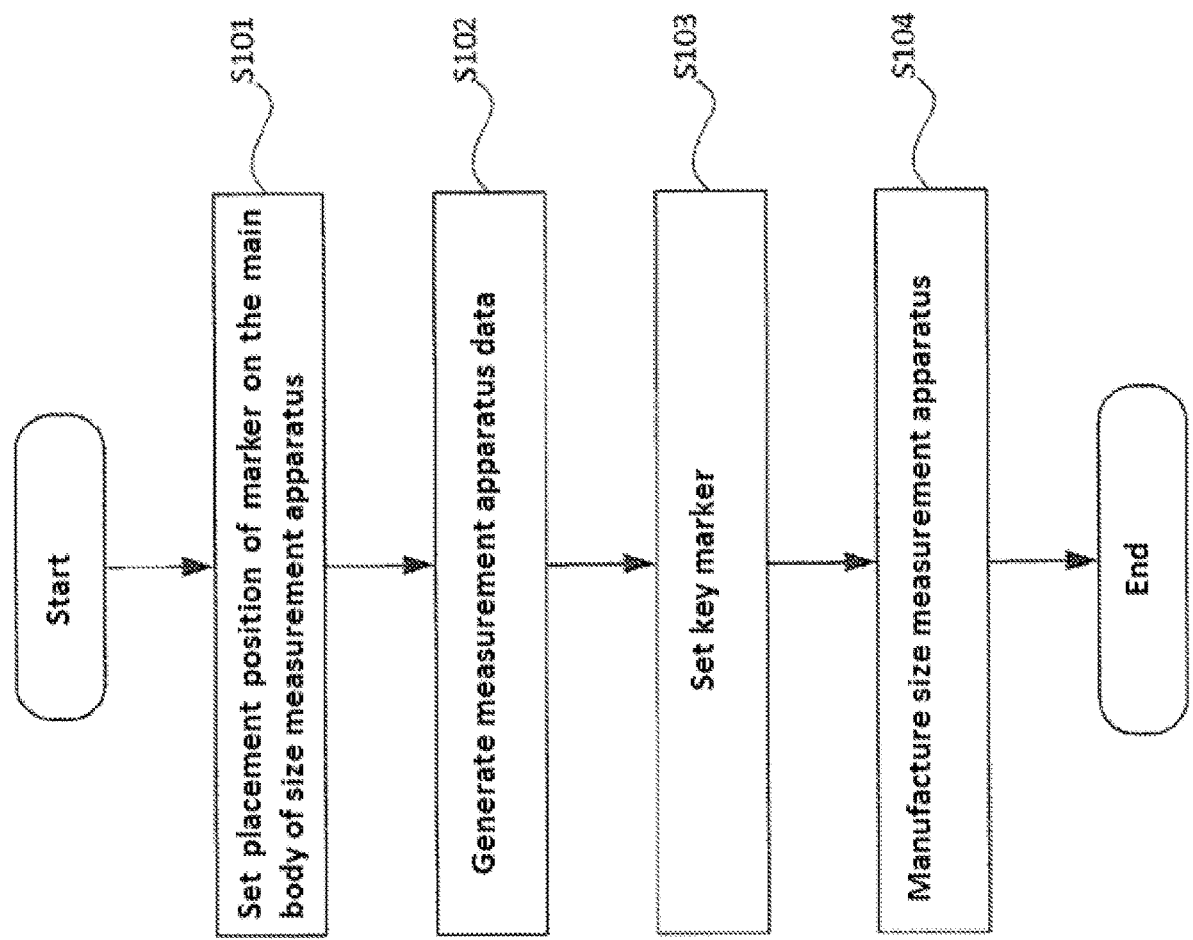

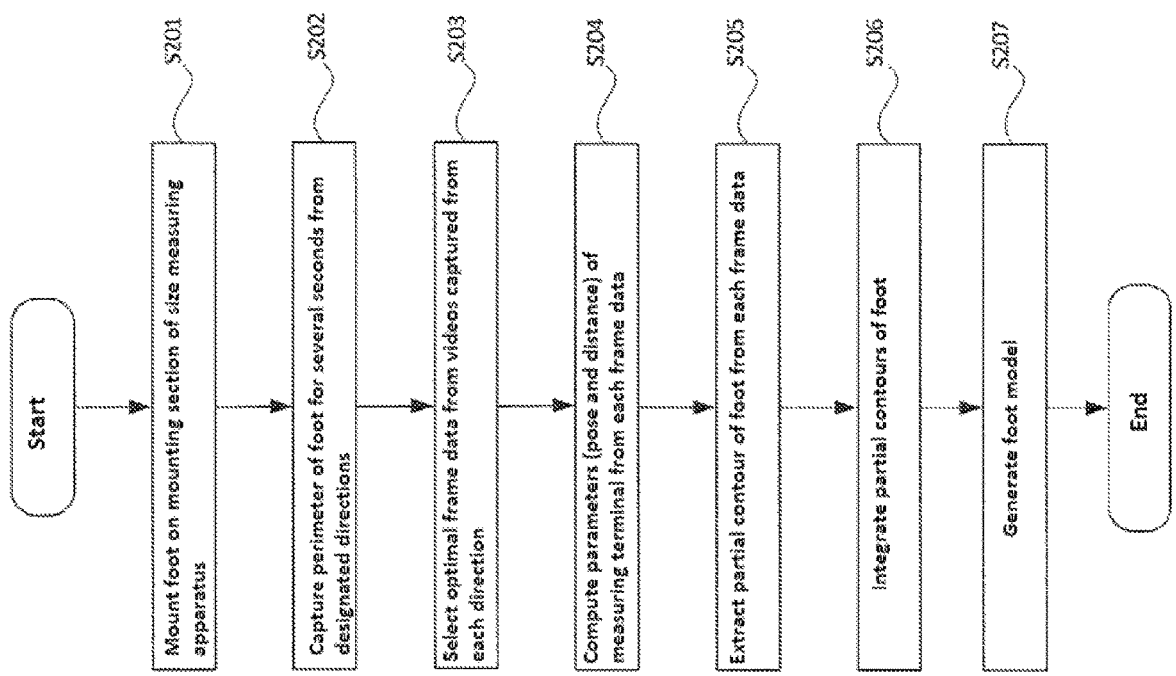

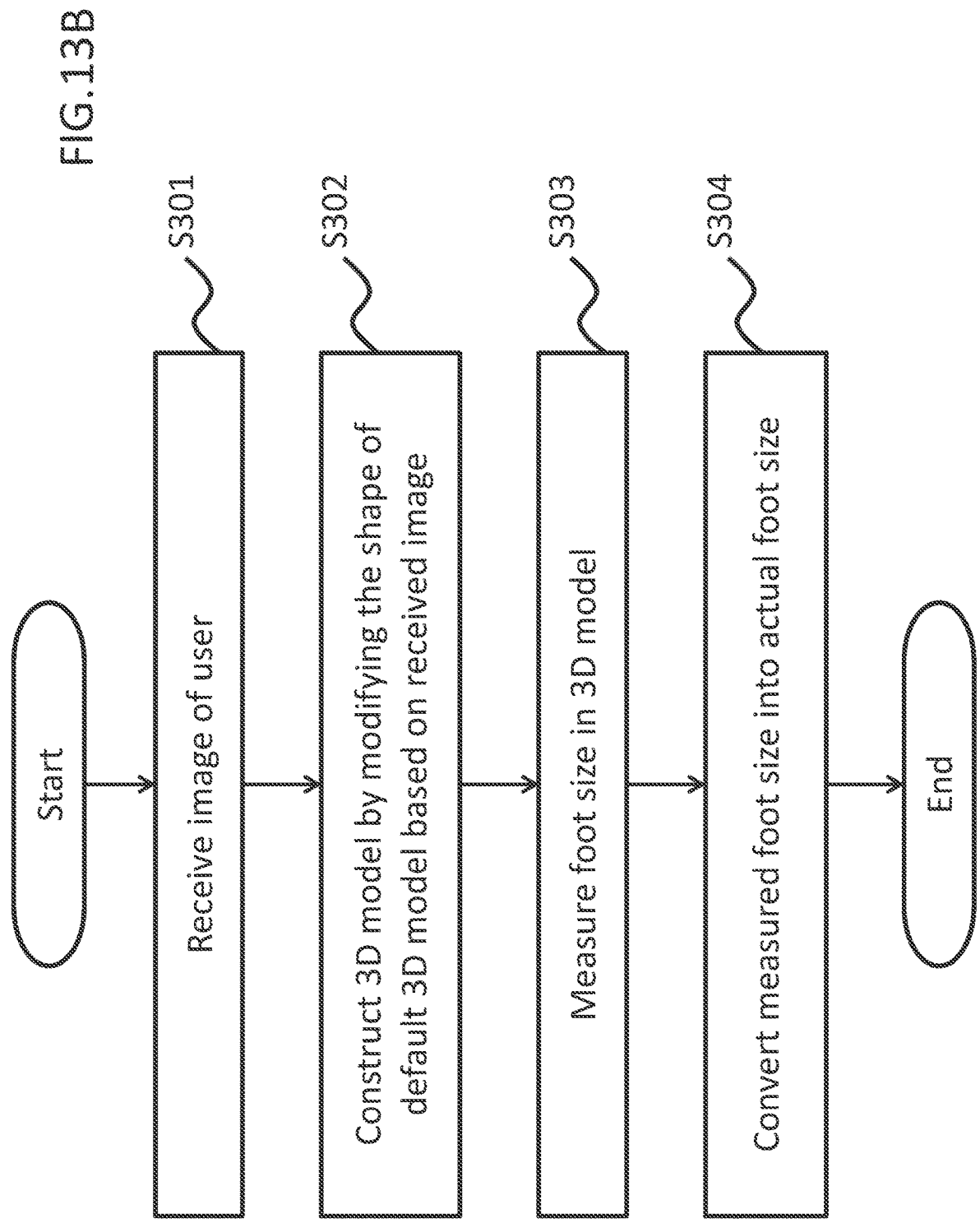

SIZE MEASUREMENT SYSTEM

TECHNICAL FIELD

The present invention relates to a size measuring system. More specifically, the present invention relates to a size measuring system for measuring the size of a three-dimensional object. In particular, the present invention relates to a size measuring system for measuring the size by capturing the three-dimensional shape of a foot.

BACKGROUND ART

In recent years, the increased prevalence of Internet technologies has resulted in electronic commerce sites providing various products, leading to continued sales growth.

Users can order a product on an electronic commerce site using a PC, mobile terminal, or the like, and then receive the product that is delivered at home without visiting a brick-and-mortar store. The number of users thereof is increasing drastically due to such convenience.

A large number of such electronic commerce sites provides apparel products such as clothes, hats, and footwear. The number of users thereof is increasing rapidly, which is approaching the number of brick-and-mortar stores.

However, among such apparel products, shoes in particular are often purchased by selecting only the user's foot size. When the purchased shoes were actually worn, the size did not match, such that the user experienced many issues such as shoe bite, foot pain, and low level of comfort.

In this regard, users can get shoes that fit their feet by going to a specialized store or the like, having the foot dimension measured by a retail employee with specialized knowledge or by measuring the foot size with a specialized measuring instrument, and ordering so-called custom-made shoes to be made.

Meanwhile, users need to go through the trouble of visiting a retail store and having the foot dimension measured. Moreover, custom-made shoes takes time to make and are more expensive than commercially available shoes, which would be a significant burden on the users.

In this regard, Patent Literature 1 discloses a technology with which users can readily measure their foot size by capturing an image or video of their feet without visiting a retail store.

The invention disclosed in Patent Literature 1 comprises mobile information device having a camera, a tilt sensor, and a processing unit, the processing unit performing a method comprising: superimposing a foot position guide image indicating a foot placement region, which is a region where a foot is placed, onto a camera image, which is an image taken by a camera by using the processing unit; detecting a tilt of the camera with respect to a given flat surface by utilizing the tilt sensor; if the tilt of the camera is at or below a predetermined threshold value for tilt, capturing a still image comprising the foot placed in the foot placement region on a flat surface and a reference article placed on a flat surface which represents a predetermined shape and size with a camera to generate image data; and calculating a dimension of the foot based on the reference article and the foot region within the image data.

CITATION LIST

Patent Literature

[PTL 1] Japanese Laid-Open Publication No. 2007-267996

SUMMARY OF INVENTION

Technical Problem

However, the invention described in Patent Literature 1 faces challenges, such as image capture being time consuming due to the need to adjust the camera tilt by the users themselves when capturing a foot, and insufficient precision to capture the complex shape of a foot due to measurement of foot size from only an image capturing the foot from above.

The present invention was conceived in view of the aforementioned challenges. The objective of the present invention is to provide a size measuring system that can measure the size of a three-dimensional object (e.g., foot) with a high level of precision by capturing a three-dimensional article mounted on a size measuring apparatus for measuring the size of the three-dimensional object.

Another objective of the present invention is to construct a 3D (three-dimensional) model reflecting the size of a three-dimensional object with a high precision in order to measure the size of the three-dimensional object with a high level of precision.

Solution to Problem

To achieve such objectives, the size measuring system of the invention is a size measuring system for measuring a size of a subject, characterized by having: a size measuring apparatus comprised of a mounting section for mounting the subject and a plurality of markers that are placed on the periphery of the mounting section; and a measuring terminal for capturing the subject being mounted on the mounting section of the size measuring apparatus so that the plurality of markers can be recognized from a plurality of directions, and computing size data of the subject from contour information on the subject obtained by capturing from each direction.

The size measuring system of the invention is characterized in that the size measuring apparatus is formed in a sheet-like form, the mounting section is placed at an approximately central portion of the sheet, and the plurality of markers are placed on the periphery of the mounting section.

The size measuring system of the invention is characterized in that the size measuring apparatus has a special marker for determining a capture direction that is placed at a predetermined position, and the measuring terminal determines a capture direction by capturing the special marker.

The size measuring system of the invention further has a provider terminal operated by a service provider providing the size measuring apparatus to a user, wherein the provider terminal is characterized by: storing marker data indicating shapes and coordinates of markers for display on the size measuring apparatus and generating measuring apparatus data for determining positions of the markers placed on the size measuring apparatus based on the marker data; and generating the size measuring apparatus based on the measuring apparatus data.

The size measuring system of the invention is characterized by comprising, at the mounting section, a pressure sensor for measuring a shape of a back side and a weight distribution of a subject.

The size measuring system of the invention is characterized in that the subject subjected to measurement is a foot.

The size measuring system of the invention further has a management server, which is connected to the measuring terminal via a network and stores a database for managing product data indicating a size of each of a plurality of footwear products that can be worn by a user, characterized in that the measuring terminal transmits the computed size data for the foot to the management server, and the management server references the database, compares the size data for the foot with sizes of plurality of products indicated by the product data, extracts product data for a product with a size, which matches with or approximates the size data for the foot of the user, and transmits the product data to the measuring terminal.

The present invention provides, for example, the following items.

(Item 1)

A computer system for measuring a size of a three-dimensional object, the computer system comprising:

receiving means for receiving an image of a three-dimensional object, the image being an image capturing the three-dimensional object mounted on a size measuring apparatus having a plurality of markers and the plurality of markers, the plurality of markers comprising a unique marker within the size measuring apparatus; and 3D model constructing means for constructing a 3D model of the three-dimensional object by modifying a shape of a default 3D model based on the default 3D model and the received image.

(Item 2)

The computer system of item 1, wherein the 3D model constructing means constructs the 3D model of the three-dimensional object by modifying the shape of the default 3D model based on a contour of the default 3D model within a virtual image obtained from the default 3D model and a contour of the three-dimensional object within the received image.

(Item 3)

The computer system of item 1 or 2, further comprising: measuring means for measuring a size in the 3D model; and converting means for converting the measured size into an actual size;

wherein the shape of the default 3D model is modified within a virtual three-dimensional space whose scale with respect to an actual three-dimensional space is predetermined, and wherein the converting means converts the measured size into an actual size by using the scale.

(Item 4)

The computer system of item 3, wherein the scale between the virtual three-dimensional space and the actual three-dimensional space is predetermined by a ratio of a size of a plurality of markers of the size measuring apparatus within the virtual three-dimensional space to a size of the plurality of markers of the size measuring apparatus within the actual three-dimensional space.

(Item 5)

The computer system of any one of items 1 to 4, further comprising capturing means for capturing the three-dimensional object, wherein the receiving means receives the image from the capturing means, and wherein the capturing means is configured to capture the three-dimensional object in response to a key marker among the plurality of markers and the three-dimensional object entering a field of view of the capturing means.

(Item 6)

The computer system of item 5, wherein the capturing means is configured at least to capture the three-dimensional object from directly above.

(Item 7)

The computer system of any one of items 1 to 6, wherein the plurality of markers have an identification element, the identification element being a plurality of dots placed in a unique pattern.

(Item 8)

The computer system of any one of items 1 to 7, wherein the three-dimensional object is a foot.

(Item 9)

A size measuring apparatus for measuring a size of a three-dimensional object, the size measuring apparatus comprising:

a mounting section for mounting the three-dimensional object; and a plurality of markers placed on the periphery of the mounting section;

wherein the plurality of markers comprise a unique marker within the size measuring apparatus.

(Item 10)

The size measuring apparatus of item 9, wherein the plurality of markers comprise at least one key marker defining a direction of capturing a three-dimensional object mounted on the mounting section.

(Item 11)

The size measuring apparatus of item 9 or 10, wherein the plurality of markers have an identification element, the identification element being a plurality of dots placed in a unique pattern.

(Item 12)

The size measuring apparatus of any one of items 9 to 11, wherein the size measuring apparatus is formed in a sheet-like form.

(Item 13)

A size measuring system comprising:

the computer system of any one of items 1 to 8; and the size measuring apparatus of any one of items 9 to 12.

(Item 14)

A program for measuring a size of a three-dimensional object, the program being executed in a computer system having a processor, wherein the program instructs the processor to perform processing comprising:

receiving an image of a three-dimensional object, the image being an image capturing the three-dimensional object mounted on a size measuring apparatus having a plurality of markers and the plurality of markers, the plurality of markers comprising a unique marker within the size measuring apparatus; and constructing a 3D model of the three-dimensional object by modifying a shape of a default 3D model based on a contour of the three-dimensional object within the received image.

(Item 15)

A method for measuring a size of a three-dimensional object, comprising:

receiving an image of a three-dimensional object, the image being an image capturing the three-dimensional object mounted on a size measuring apparatus having a plurality of markers and the plurality of markers, the plurality of markers comprising a unique marker within the size measuring apparatus; and constructing a 3D model of the three-dimensional object by modifying a shape of a default 3D model based on a contour of the three-dimensional object within the received image.

(Item 16)

A size measuring system for measuring a size of a three-dimensional object, having:

a size measuring apparatus comprised of a mounting section for mounting a three-dimensional object, and a plurality of markers that are placed on the periphery of the mounting section; and a measuring terminal for capturing the three-dimensional object being mounted on the mounting section of the size measuring apparatus so that the plurality of markers can be recognized from a plurality of directions, and computing size data for the three-dimensional object from contour information on the three-dimensional object obtained by capturing from each direction.

(Item 17)

The size measuring system of item 16, wherein the size measuring apparatus is formed in a sheet-like form, the mounting section is placed at an approximately central portion of the sheet, and the plurality of markers are placed on the periphery of the mounting section.

(Item 18)

The size measuring system of item 16 or 17, wherein the size measuring apparatus has a special marker for determining a capture direction that is placed at a predetermined position, and the measuring terminal determines a capture direction by capturing the special marker.

(Item 19)

The size measuring system of any one of items 16 to 18, further having a provider terminal operated by a service provider providing the size measuring apparatus to a user, wherein the provider terminal is characterized by:

storing marker data indicating shapes and coordinates of markers for display on the size measuring apparatus and generating measuring apparatus data for determining positions of the markers placed on the size measuring apparatus based on the marker data; and generating the size measuring apparatus based on the measuring apparatus data.

(Item 20)

The size measuring system of any one of items 16 to 19, comprising, at the mounting section, a pressure sensor for measuring a shape of a back side and a weight distribution of a three-dimensional object.

(Item 21)

The size measuring system of any one of items 16 to 20, wherein the three-dimensional object is a foot.

(Item 22)

The size measuring system of item 21, further having a management server, which is connected to the measuring terminal via a network and stores a database for managing product data indicating a size of each of a plurality of footwear products that can be worn by a user, wherein the measuring terminal transmits the computed size data for the foot to the management server; and the management server references the database, compares the size data for the foot with sizes of plurality of products indicated by the product data, extracts product data for a product with a size, which matches with or approximates the size data for the foot of the user, and transmits the product data to the measuring terminal.

(Item 23)

A computer system for measuring a size of a three-dimensional object, the computer system comprising:

receiving means for receiving an image of a three-dimensional object, the image being an image capturing the three-dimensional object and a plurality of markers, the plurality of markers comprising a unique marker; and 3D model constructing means for constructing a 3D model of the three-dimensional object by modifying a shape of a default 3D model based on the received image.

Advantageous Effects of Invention

In this manner, the present invention can provide a size measuring system that can measure the size of a three-dimensional object, readily and with a high level of precision, by capturing an image from a plurality of directions.

The present invention also enables construction of a 3D model reflecting the size of a three-dimensional object with high precision in order to measure the three-dimensional object with a high level of precision.

BRIEF DESCRIPTION OF DRAWINGS

FIG. 4A is a diagram showing the configuration of a measuring terminal.

FIG. 5 is a diagram showing data or the like stored by an information storage unit 22 of a measuring terminal 20.

FIG. 6 is a diagram showing an example of a data configuration of a marker DB 221.

FIG. 11 is a diagram showing an example of a data configuration of a product DB.

FIG. 12 is a flowchart showing the flow of the manufacture of a size measuring apparatus.

FIG. 13A is flowchart showing a method of measuring a foot size of a user.

FIG. 13B is flowchart showing an example of processing for measuring the foot size of a user.

DESCRIPTION OF EMBODIMENTS

Figure 1:
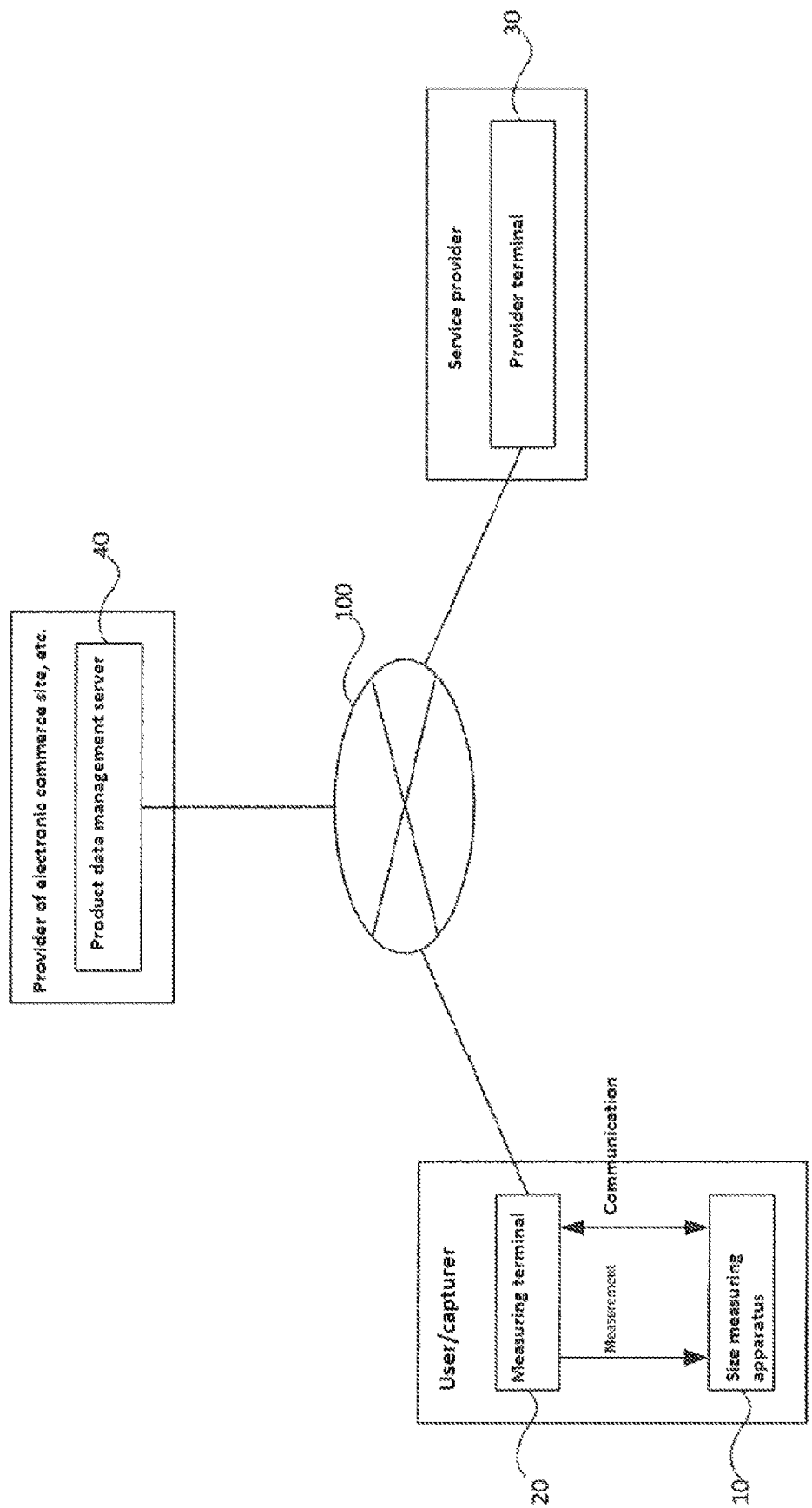
FIG. 1 is a diagram showing the configuration of a size measuring system.

The size measuring system according to this embodiment is now described while referring to the drawings.

FIG. 1 is a diagram showing the configuration of a size measuring system.

As illustrated, the size measuring system comprises a size measuring apparatus 10 on which a foot of a user is mounted for measuring the size of the foot of the user, and a measuring terminal 20 for measuring the size of the foot by capturing the foot of the user being mounted on the size measuring apparatus 10. The size measuring system can further comprises a provider terminal 30 operated by a service provider providing the size measuring apparatus 10, and a product data management server 40 for storing a database for product data comprising size information on footwear desired by the user or the like. The terminal device 20, provider terminal 30, and data management server 40 are each connected to a network 100 and can communicate with one another via the network 100.

<Size Measuring Apparatus 10>

Figure 2:
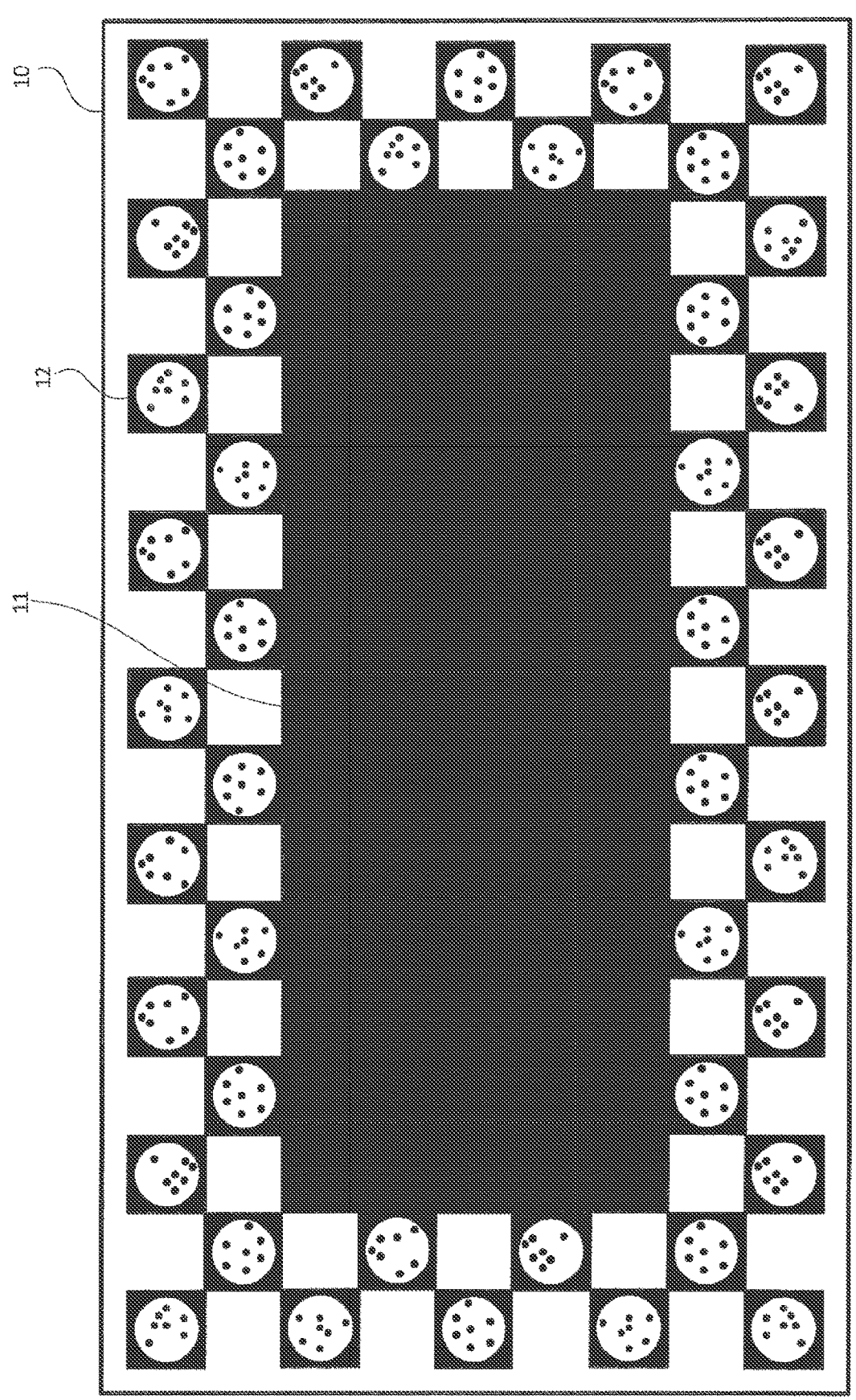
FIG. 2 is a diagram showing the configuration of a size measuring apparatus.
Figure 3:
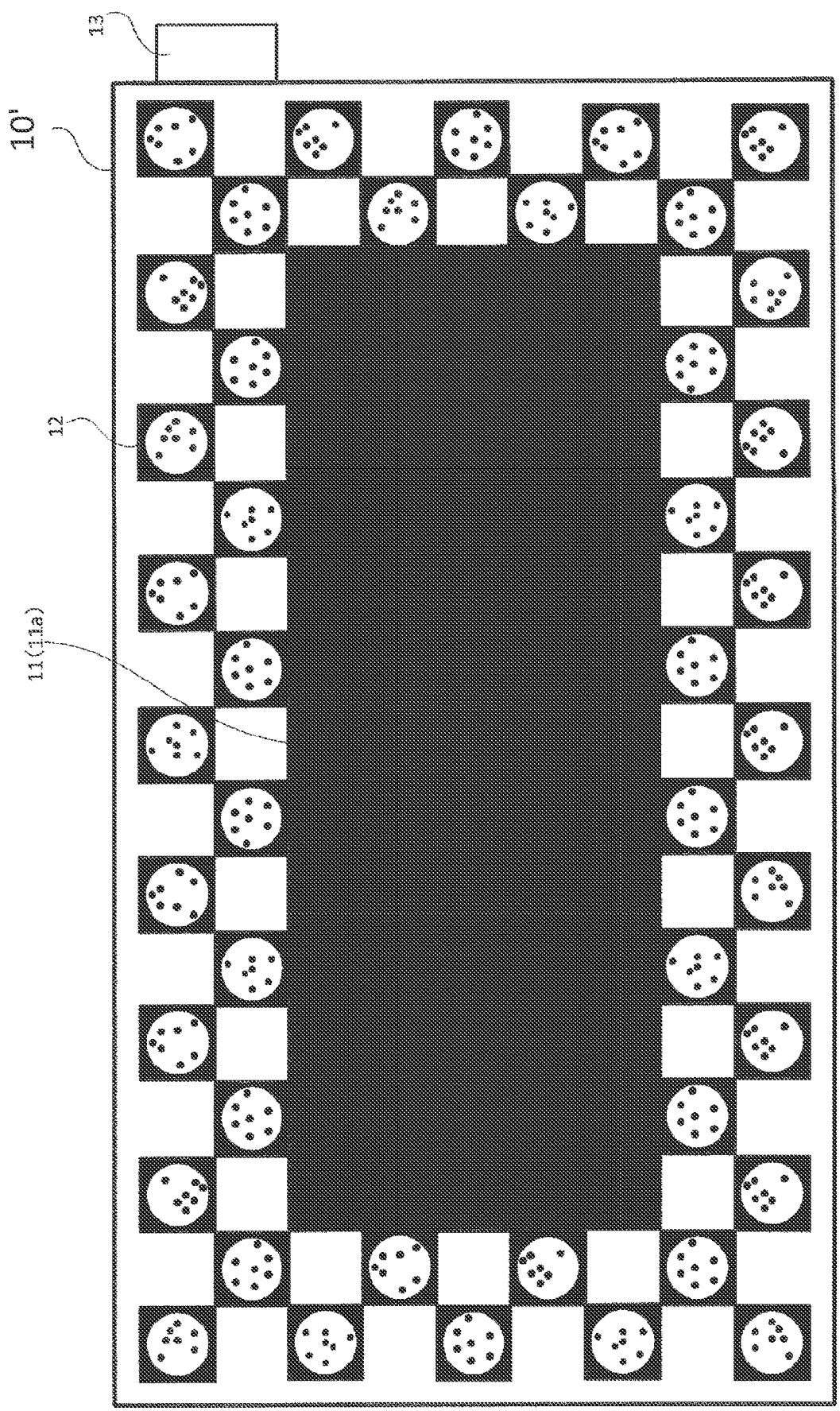
FIG. 3 is a diagram showing another configuration of a size measuring apparatus.

FIG. 2 is a diagram showing the configuration of the size measuring apparatus 10 according to one embodiment. FIG. 3 is a diagram showing the configuration a size measuring apparatus 10' according to another embodiment.

As illustrated, the size measuring apparatuses 10, 10' are formed in an approximately rectangular sheet-like form or mat-like form, which can be mounted on the floor, ground, or the like. The apparatuses is made of a material that can be processed into paper, cloth, or sheet-like form. An approximately rectangular mounting section 11 for a user to mount a foot is displayed (or printed) at an approximately central portion of the sheet-like surface, and a plurality of identifiable markers 12 arranged in a grid pattern are displayed (or printed) in the perimeter of the mounting section 11

The shape of the main body of the size measuring apparatus 10 is not limited to an approximately rectangular shape. The shape can be an approximately polygonal or approximately circular shape.

The mounting section 11 is formed in an approximately rectangular shape as described above, with a length and width that would roughly fit a normal foot size (about 29.0 cm). The mounting section 11 is configured to have a color other than the skin color to facilitate distinction of the boundary from the mounted foot.

The shape, size, surface design (pattern), color tone, material, and the like of the markers 12 are not particularly limited. Various shapes, sizes, surface designs (patterns), color tones, materials, and the like can be applied. Each of the plurality of markers 12 can be a non-unique marker within the size measuring apparatus 10, or a unique marker within the size measuring apparatus 10 as described below.

For the markers 12, different shapes, sizes, surface designs (patterns), color tones, materials, and the like can be used in each of the markers 12 to identify each of the markers 12. Each element for identifying such markers individually is referred to as an "identification element" hereinafter. Each of the markers 12 has an individually different identification element, which renders each of the markers 12 unique within the size measuring apparatus 10.

The measuring terminal 20 identifies each of the markers 12 by reading out an identification element of these markers 12 by an optical readout method or the like. The identification element can be any element, as long as the element can be recognized during image processing. The identification element can be, for example, a plurality of dots placed in a unique pattern in each marker, or color applied in each marker (including, for example, cases where a color is applied over the entire surface of a marker, cases where a plurality of colors are applied for each region in the marker to form a unique marker as a whole, and the like). A preferred identification element in the present invention can be a plurality of dots placed in a unique pattern in each marker. For example, the dots in the markers can have a maximum dimension of about 5% to 15% of the maximum dimension of the marker. For example, if the plurality of markers 12 are circular with a diameter of about 20 mm, the dots can be circular with a diameter of about 1 mm to about 3 mm. Since the unique pattern of dots can be expanded infinitely by changing the number and position of dots, the number of plurality of markers 12 on the size measuring apparatus 10 can be readily increased or decreased. This enables the size measuring apparatus 10 to be readily expanded or contracted.

Users can measure the size of a foot (length, width, and instep height) by mounting their own foot on the mounting section 11 of the size measuring apparatus 10 and capturing the foot being mounted to include the markers 12 from a plurality of directions with the measuring terminal 20.

The size measuring apparatus 10' in another embodiment shown in FIG. 3 is the same as the size measuring apparatus 10 in the embodiment shown in FIG. 2, except for further comprising a pressure sensor 11a and a communication unit 13. The shape of the bottom of the foot of a user or the extent of body weight applied can be detected by: providing an elastic article (not shown), which is elastically deformable especially in the direction of thickness and is made of an elastic material such as rubber or resin, and the pressure sensor 11a connected to the elastic article to the mounting section 11 of the size measuring apparatus 10 as shown in FIG. 3; and detecting the extent of depression of the mounted portion with the pressure sensor 11a when the user mounts the foot on the elastic article. The measurement results can be transmitted to the measuring terminal 10 from the communication unit 13.

The communication unit 13 can communicate in a wired manner or wirelessly. The communication unit 13 can perform near field communication such as Bluetooth® or Wi-Fi.

While examples utilizing the size measuring apparatus 10 are described hereinafter, it is obviously understood that the size measuring apparatus 10' can also be utilized in the same manner.

<Measuring Terminal 20>

The configuration of the measuring terminal 20 is now described while referring to FIG. 4.

FIG. 4 is a diagram showing the configuration of the measuring terminal 20.

The measuring terminal 20 is an information processing device that is operated when measuring the foot size of a user.

For example, the measuring terminal 20 is a mobile information processing device such as a smartphone, tablet terminal, wearable terminal, mobile phone, PDA, PHS, or PC.

Users mount their own foot on the mounting section 11 of the size measuring apparatus 10, and capture the foot being mounted using the measuring terminal 20. At this time, the users capture their own foot from a plurality of directions so that the plurality of markers 12 would be within the image. This allows the measuring terminal 10 to know the capture position of the measuring terminal 10 when capturing images from a plurality of directions by recognizing each of the plurality of markers 12, and the foot size of the users to be measured by combining the capture position and the captured image.

The measuring terminal 20 can also communicate with the product data management server 40 via a network using a communication function to search for a footwear product matching the size of the foot based on the measured foot size of the user.

As shown in FIG. 4, the measuring terminal 20 is comprised of: a control unit 21 for controlling the entire measuring terminal 20, composed of a CPU or the like; an information storage unit 22 for storing various pieces of information; a communication unit 23 for communicating with the product data management server 40 via a network 100; a display unit 24 for displaying various pieces of information; an operation unit 25 used for inputting information, comprising various keys and the like; and a capture unit 26 for inputting an image, comprising a camera or the like.

The display unit 24 and the operation unit 25 can also be integrally constructed as a touch panel. Furthermore, each of the units 21 to 26 is connected to an internal bus. Various pieces of information and the like are inputted and outputted via such a bus. Various processes are executed under the control of the control unit 21.

The control unit 21 is a processing unit responsible for controlling the entire measuring terminal 20, and is composed of an electric circuit such as a CPU (Central Processing Unit) or an integrated circuit such an FPGA (Field-Programmable Gate Array). The control unit 21 executes readout of information from the information storage unit 22 as well as write-in of information into the information storage unit 22.

The information storage unit 22 is a device for storing information, such as a hard disk, memory, or a semiconductor element. The information storage unit 22 has a region for storing a program executed by the control unit 21 (e.g., program materializing at least a part of the processing shown in FIGS. 13A, 13B, and 13C), a working region (RAM or the like) that is temporarily used when the control unit 21 executes a process, or the like.

The control unit 21 reads out a program stored in the information storage unit 22 (three-dimensional reconstruction algorithm, optimization algorithm, bundle adjustment algorithm, or the like) and deploys the program in the working region to execute various processes.

A marker data DB indicating the placement positions of the markers 12 displayed on the size measuring apparatus 10 is stored in the information storage unit 22 in advance. The information storage unit 22 can further store foot model data representing a common foot model in advance. Such marker data and foot model DBs are generated by the provider terminal 30 in a manner described below.

For example, the information storage unit 22 can store data for constructing a 3D model, generated by the 3D model constructing means 211 described below. Data for constructing a 3D model can be data for expressing a 3D model that is known in the art. Data can be, for example, polygon data representing each vertex of a 3D model. Specifically, the contour of the 3D model can be represented by a plurality of vertices. Alternatively, the counter of the 3D model can be represented by a straight or curved line, or a flat or curved surface passing through a plurality of vertices.

The information storage unit 22 can further store data for constructing a default 3D model. A default 3D model is a base 3D model used for constructing a 3D model of a subject. A default 3D model preferably has a shape that roughly mimics the shape of the subject. This is because this can facilitate convergence of processing for constructing a 3D model by the 3D model constructing means 211 described below. For example, as the base default 3D model for constructing a 3D model of a foot of a user, a different model can be selected for each target user, or the model can be constant for each user. If the base default 3D model is constant for each user, a default 3D model can be constructed, for example, as a model having a foot length of about 25 cm.

Data for constructing a default 3D model can be data for expressing a 3D model that is known in the art. Data can be, for example, polygon data representing each vertex of a 3D model. Specifically, the contour of a default 3D model can be represented by a plurality of vertices. Alternatively, the contour of a default 3D model can be represented by a curved line or curved surface passing through a plurality of vertices.

The communication unit 23 is an interface for controlling the communication with the product data management server 40 via the network 100, having a LAN adapter or the like.

The communication unit 23 can comprise a wireless transceiver and be connected to a LAN, Internet, or the like via wireless communication, or can be connected via a wire such as a cable.

The display unit 24 is a display device such as a display or a lamp.

The control unit 21 reads out an image from the information storage unit 22, and executes image output processing to generate screen information. The control unit also executes image output processing on image information received by the communication unit 23 from the product data management server 40 to generate screen information.

The control unit 21 also outputs the generated image information to the display unit 24, and the display unit 24 displays the inputted image information on a screen such as a display.

The control unit 21 can also output a control signal to the display unit 24 and light up a lamp of the display unit 24.

The operation unit 25 comprises an information input device composed of, for example, various keys or the like. The information input device provides a pointing device in cooperation with the display unit 24. The operation unit 25 accepts various operations from a user or the like and outputs a signal indicating the specific operation to the control unit 21.

When the signal indicating the specific operation is inputted, the control unit 21 outputs, on the display unit 24, a control signaling instructing to display a screen on the display unit 24 in accordance with the specific operation in accordance with the content of the signal.

When the control signal is inputted, the display unit 24 displays a screen in accordance with the control signal.

The display unit 24 and the operation unit 25 can also be integrally constructed as a touch panel.

The capture unit 26 comprises a camera or the like that can capture a still image or a video. A user can capture a foot being mounted on the mounting section 11 of the size measuring apparatus 10 by utilizing the capture unit 26. For example, users can set the capture unit 26 to a video mode that can capture a video, and capture a video of their own foot mounted on the mounting section 11 of the size measuring apparatus 10 for several seconds from a plurality of directions so that a plurality of markers would be captured.

The capture unit 26 inputs video data that has captured a video into the control unit 21. The framerate of video data can be any framerate, such as 10 fps, 20 fps, 30 fps, or 60 fps. For example, the control unit 21 can select optimally captured frame data from a plurality of pieces of frame data in the video data captured for each of the plurality of directions. For example, the control unit 21 can select frame data with the least amount of blur among a plurality of pieces of frame data. For example, the control unit 21 can select frame data with the best focus among a plurality of pieces of frame data.

The control unit 21 then recognizes an image of the plurality of markers 12 placed on the size measuring apparatus 10 from the selected frame data, and recognizes which marker 12 is at which position of a planar space indicated in the frame data.

The control unit 21 also recognizes the contour of the size measuring apparatus 10 (boundary from the background) and the contour of a foot mounted on the mounting section (boundary between the mounting section 11 and the foot) in addition to an image of the markers 12 in the frame data. The image recognition methodology used by the control unit can be, for example, conventional, common optical readout methodology or methodologies using other image recognition methods.

The control unit 21 computes the pose information (angles in each capture direction of yaw, pitch, and roll) and distance information of the measuring terminal 20 by using the principle of triangulation, based on recognition of each marker 12 and the planar coordinates in the planar space.

The control unit 21 also extracts partial contour data for each foot from frame data from each direction and forms foot contour data constituting the entire foot from the pose information and distance information on the measuring terminal 20 and the partial contour data.

Furthermore, the control unit 21 computes the optimal foot size measurement data by combining such contour data with foot model data described below.

In another example, once an image capturing a foot of a user on the size measuring apparatus 10 is received from the capture unit 26, the control unit 21 can generate contour data based on the received image and construct a 3D model of the foot of the user (foot model) based on the contour data. The control unit 21 can compute foot size measurement data by measuring the dimension on the 3D model.

Figure 4B:
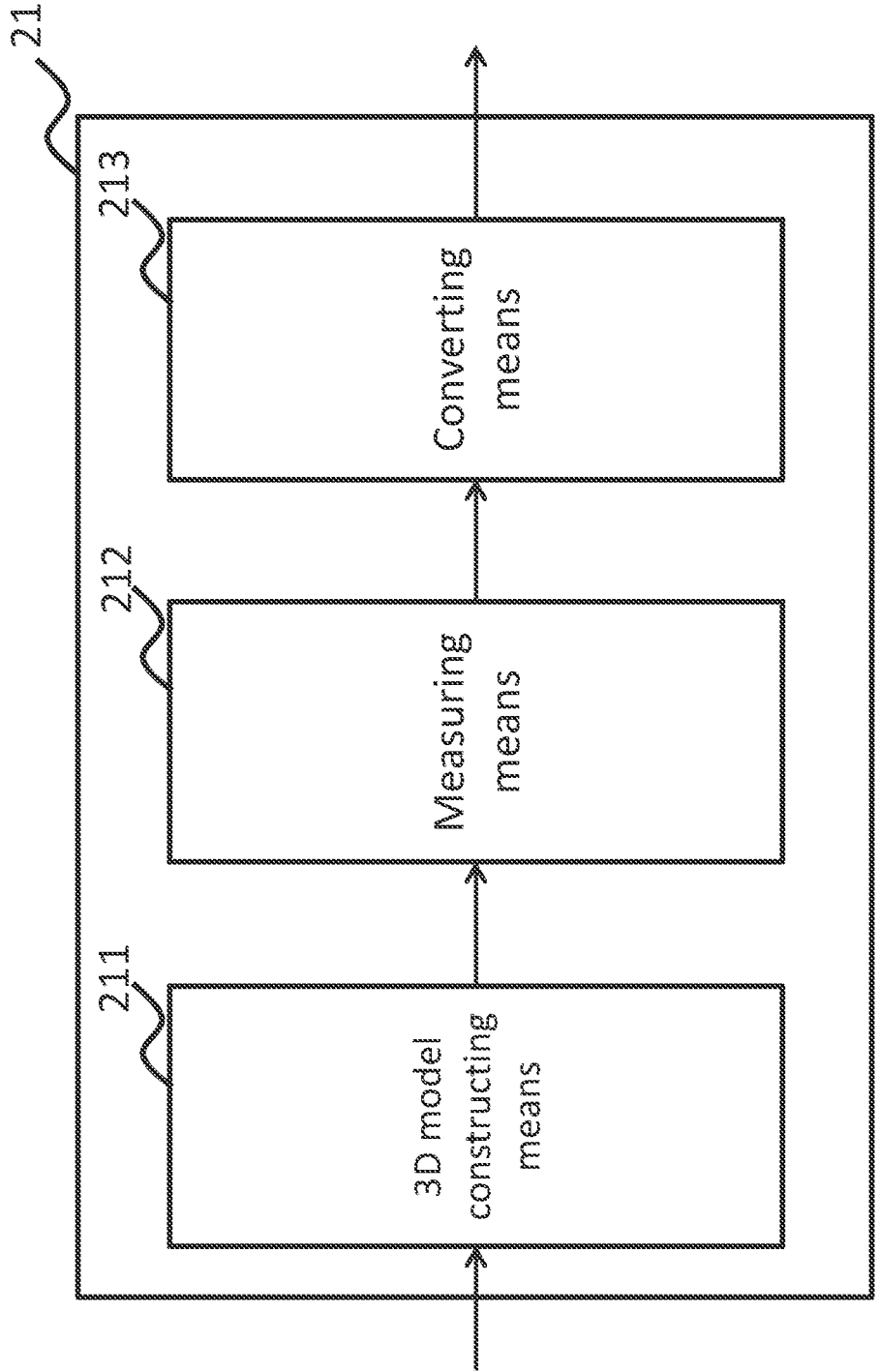
FIG. 4B is a diagram showing an example of the configuration of control unit 21.

FIG. 4B is a diagram showing an example of the configuration of the control unit 21 according to this example.

The control unit 21 can comprise at least 3D model constructing means 211.

The 3D model constructing means 211 is configured to receive an image captured using the capture unit 26 and construct a 3D model based on the received image. The 3D model constructing means 211 can construct a 3D model of a user, for example, by modifying the shape of a default 3D model based on the received image.

In one example, the 3D model constructing means 211 can obtain a two-dimensional virtual image from a default 3D model, and modify the shape of the default 3D model based on the contour of the default 3D model on the virtual image obtained from the default 3D model and the contour of a foot on a received image. The virtual image is an image virtually capturing the default 3D model from a plurality of directions. The capture direction of a virtual image can be the same direction as the direction from which an image is captured by the measuring terminal 20, and the capture position of a virtual image can be the same position as the direction from which an image is captured by the measuring terminal 20. This is because this allows the contour of a default 3D model on a virtual image to be compared with the contour of a foot on a received image. The capture direction and capture position of the measuring terminal 20 can be computed using the principle of triangulation, based on the planar coordinates in a planar space of each marker 12 recognized within frame data.

For example, the 3D model constructing means 211 computes a discrepancy between the contour of a default 3D model on a virtual image and the contour of a foot on a received image, and performs a default 3D model based modification such that the computed discrepancy is minimized. For example, the 3D model constructing means 211 computes the discrepancy between a plurality of vertices representing the contour of a default 3D model on a virtual image and a plurality of vertices representing the contour of a foot on a received image, determines the positions of vertices on the default 3D model on the virtual image that minimize the computed discrepancy, and moves the vertices of the base default 3D model so that the vertices are at the determined positions. A 3D model constructed based on the default 3D model to minimize the discrepancy between the contour of the default 3D model on virtual images captured from a plurality of directions and the contour of the foot on images actually captured from a plurality of directions would be the 3D model of a user. In this regard, it is not necessary that the discrepancy is completely 0. The discrepancy can be a specific minimum value (e.g., fixed value, or a value less than or equal to a predetermined threshold value). The 3D model constructing means 211 can derive a modification that minimizes the computed discrepancy by any approach. For example, a modification that minimizes the computed discrepancy can be derived using the least square method.

The shape of a default 3D model can be modified by the 3D model constructing means 211 within a virtual three-dimensional space. A virtual three-dimensional space is a space that is created by expanding or contracting an actual three-dimensional space at a predetermined scale. With modification of shape within a virtual three-dimensional space, the scale is unchanged before and after the modification, so that computation of the size within an actual three-dimensional space using a 3D model after the modification of shape and the scale is facilitated.

For example, the scale between a virtual three-dimensional space and an actual three-dimensional space is predetermined by the ratio of the size of the plurality of markers 12 of the size measuring apparatus 10 within the virtual three-dimensional space to the size of the plurality of markers 12 on the size measuring apparatus 10 within the actual three-dimensional space. For example, if the size of the plurality of markers 12 of the size measuring apparatus 10 within a virtual three-dimensional space is X, and the size of the plurality of markers 12 on the size measuring apparatus 10 within an actual three-dimensional space is Y, the scale is determined as X:Y.

The control unit 21 can further comprise measuring means 212 and converting means 213.

The measuring means 212 is configured to measure the size in a 3D model of a user constructed by the 3D model constructing means 211. The size measured by the measuring means 212 is the size within a virtual three-dimensional space. The measuring means 212 can measure the size of a 3D model using a known methodology. For example, the measuring means 212 can determine the size of a site targeted for measurement by slicing a 3D model into a two dimensional cross-section and measuring the dimension of the site targeted for measurement in the two-dimensional cross-section. For example, the foot length can be measured by measuring the length between the heel and the toe in a two-dimensional cross-section passing through the heel and the toe. For example, the foot circumference can be measured by measuring the circumferential length in a two-dimensional cross-section passing through the base of the big toe and base pf the pinky toe.

The converting means 213 is configured to convert the size measured by the measuring means 212 into the actual foot size. As described above, the size measured by the measuring means 212 is the size within a virtual three-dimensional space, so that such a size needs to be converted into the size within the actual three-dimensional space by the converting means 213. For example, the converting means 213 converts the size within a virtual three-dimensional space into the size within an actual three-dimensional space using the scale between the virtual three-dimensional space and the actual three-dimensional space.

The control unit 21 computes measurement size data representing the size of a given foot part of a user based on the size within the actual three-dimensional space outputted by the converting means 213.

The control unit 21 can output the computed foot size measurement data to the display unit 24 and display the data on the display unit 24.

This enables a user to check and reference the displayed foot size measurement data when purchasing footwear that matches the user's own foot size.

The measuring terminal 20 can receive screen information, e.g., a web page, from the product data management server 40 that functions as a web server, and display the information.

The measuring terminal 20 has a function of generating and transmitting an HTTP (Hyper Text Transfer Protocol) request in response to a user request and a function for interpreting the HTTP response (an example of a response) and presenting the response to a user by the control unit 21.

For example, the information storage unit 22 stores a web browser as an example. The control unit 21 interprets an HTTP response and presents the HTTP response to a user by generating image data or audio data, displaying the data on the display unit 24, or outputting an audio from a speaker of the measuring terminal 20.

When the communication unit 23 transmits measurement data indicating the foot size of a user to the product data management server 40, the product data management server 40 extracts data for a product (product data) matching the foot size indicated by the measurement data from a database (product DB 421) and transmits product search result information (web page or the like), which is screen information including the product data, to the measuring terminal 20.

The communication unit 23 of the measuring unit 20 displays the product search result information on the display unit 24 when the information is received from the product data management server 40. Users can readily find product information on footwear that matches their own foot size by looking at the displayed product search result information. This facilitates the selection of a product to be purchased.

If product search result information is on a web page of an electronic commerce site, a user can directly purchase the product on the electronic commerce site by operating the operation unit 25 and pointing out (clicking a button or the like) a given area of the product search result information displayed on the display unit 24.

FIG. 5 is a diagram showing data or the like stored by the information storage unit 22 of the measuring terminal 20.

The information storage unit 22 stores a marker DB 221 for managing identification elements such as the shape of each marker 12. As illustrated, the information storage unit 22 can also store a foot model DB 222 that indicates a plurality of sizes FIG. 6 is a diagram showing an example of a data configuration of the marker DB 221.

As illustrated, the marker DB 221 manages text data or image data indicating the shape, size, surface design (pattern), color tone, material, or the like of the markers for each marker. A key marker that can define the direction from which the measuring terminal 20 captures an image when an image is captured is determined from among the plurality of markers 12.

The control unit 21 of the measuring terminal 20 can recognize and identify the image of the captured markers 12 by referring to the marker DB 221. The control unit 21 of the measuring terminal 20 can also recognize a captured key marker and identify the capture direction.

The foot model DB 222 is data for a foot model representing a common foot shape as a three-dimensional model expressing the foot surface. The foot model data prepares various three-dimensional models with different foot lengths, widths, and instep heights. The control unit 21 of the measuring terminal 20 can compute foot size measurement data by combining contour data with approximate foot model data.

In another example, the foot model DB 222 can comprise data for constructing a 3D model of a foot of a user and data for constructing a default 3D model.

<Provider Terminal 30>

The provider terminal 30 is an information processing device operated by a service provider providing the size measuring apparatus 10 to users.

For example, the provider terminal 30 is an information processing device such as a PC, tablet terminal, smartphone, wearable terminal, mobile phone, PDA, or PHS. The provider terminal 30 generates measuring apparatus data by setting the placement positions of the markers 12 of the size measuring apparatus 10, and generates measuring apparatus data with set placement positions of the markers 12.

The provider terminal 30 generates the size measuring apparatus 10 based on measuring apparatus data comprising three-dimensional coordinates of a displayed virtual group of points of the size measuring apparatus 10. The generation method thereof is not particularly limited. A conventional method can be used for the generation.

Figure 7:
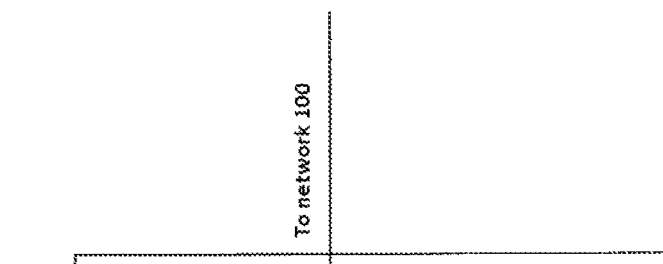
FIG. 7 is a diagram showing the configuration of a provider terminal 30.

FIG. 7 is a diagram showing a configuration of the provider terminal 30.

As illustrated, the provider terminal 30 is comprised of a control unit 31 for controlling the entire provider terminal 30 composed of a CPU or the like, an information storage unit 32 for storing various pieces of information, a communication unit 33 for performing communication, a display unit 34 for displaying various pieces of information, and an operation unit 35 used for inputting information, comprising various keys and the like.

The display unit 34 and the operation unit 35 can also be integrally constructed as a touch panel.

Each of the units 31 to 35 is connected to an internal bus. Various pieces of information and the like are inputted and outputted via such a bus. Various processes are executed under the control of the control unit 31.

The control unit 31 is a processing unit responsible for controlling the entire provider terminal 30, composed of an electric circuit such as a CPU (Central Processing Unit) or an integrated circuit such an FPGA (Field-Programmable Gate Array).

The control unit 31 executes readout of information from the information storage unit 32 as well as write-in of information into the information storage unit 32.

The information storage unit 32 is a device for storing information, such as a hard disk, memory, or a semiconductor element.

The information storage unit 32 has a region for storing a program executed by the control unit 31 or a working region (RAM or the like) that is temporarily used when the control unit 31 executes a process.

The control unit 31 reads out a program stored in the information storage unit 32 and deploys the program in a working region to execute various processes.

The communication unit 33 is an interface for controlling communication, having a LAN adapter or the like.

The communication unit 33 can also comprise a wireless transceiver and be connected to LAN, Internet, or the like via wireless communication, or can be connected via a wire such as a cable.

The display unit 34 is a display device such as a display or a lamp.

The control unit 31 reads out an image from the information storage unit 32, and executes image output processing to generate screen information. The control unit 31 also executes image output processing on image information received by the communication unit 33 from the product data management server 40 to generate screen information.

The control unit 31 can also output the generated image information to the display unit 34 and light up a lamp of the display unit 34.

The operation unit 35 comprises an information input device composed of, for example, various keys or the like. The information input device provides a pointing device in cooperation with the display unit 34. The operation unit 35 accepts various operations by a user or the like and outputs a signal indicating a specific operation to the control unit 31 or the like.

When the signal indicating the specific operation is inputted, the control unit 31 outputs, on the display unit 34, a control signaling instructing to display a screen on the display unit 34 in accordance with the specific operation in accordance with the content of the signal.

When the control signal is inputted, the display unit 34 displays a screen in accordance with the control signal.

The display unit 34 and the operation unit 35 can also be integrally constructed as a touch panel.

Figure 8:
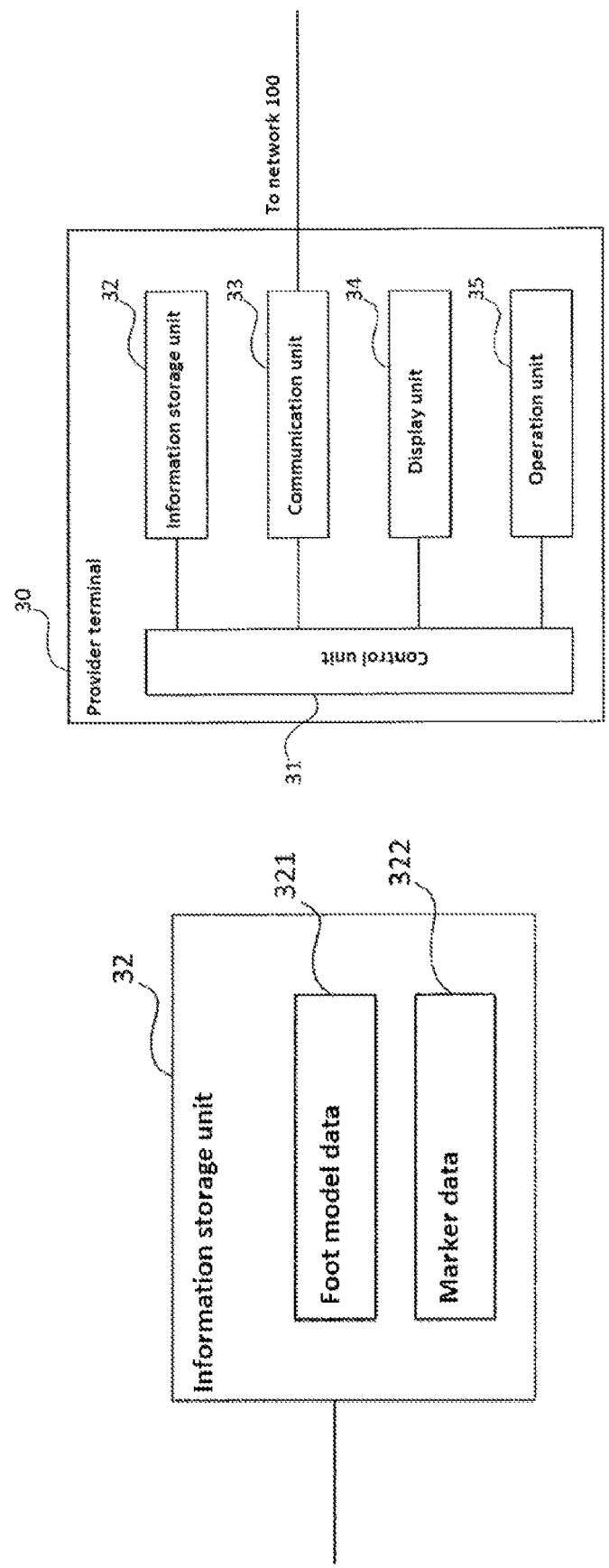
FIG. 8 is a diagram showing data or the like stored by an information storage unit 32 of the provider terminal 30.

FIG. 8 is a diagram showing data or the like stored by the information storage unit 32 of the provider terminal 30.

As illustrated, the information storage unit 32 stores foot model data 321 and marker data 322.

The foot model data 321 is data for a foot model representing a common foot shape as a three-dimensional model expressing the foot surface. The foot model data prepares various three-dimensional models with different foot lengths, widths, and instep heights.

A plurality of patterns of foot models can be prepared in advance by sex, age, race, or the like. In such a case, the information storage unit 32 stores foot data corresponding to the plurality of patterns.

The marker data 322 is aggregation of three-dimensional coordinates of a virtual group of points indicating the shape of the markers 12 or the like.

The control unit 31 of the provider terminal 30 can generate, and display on the display unit 34, a three-dimensional image of a foot model and the markers 12 based on three-dimensional coordinates of a group of points constituting the foot model data 321 and marker data 322, respectively.

This is materialized by a common and conventional technique of processing for displaying three-dimensional images using point group data.

<Product Data Management Server 40>

The product data management server 40 is a server for managing product data for footwear and generating and providing a web page for selling the footwear.

The product data management server 40 is managed, for example, by an electronic commerce site operator or the like engaging in the business of selling footwear on the Internet.

Figure 9:
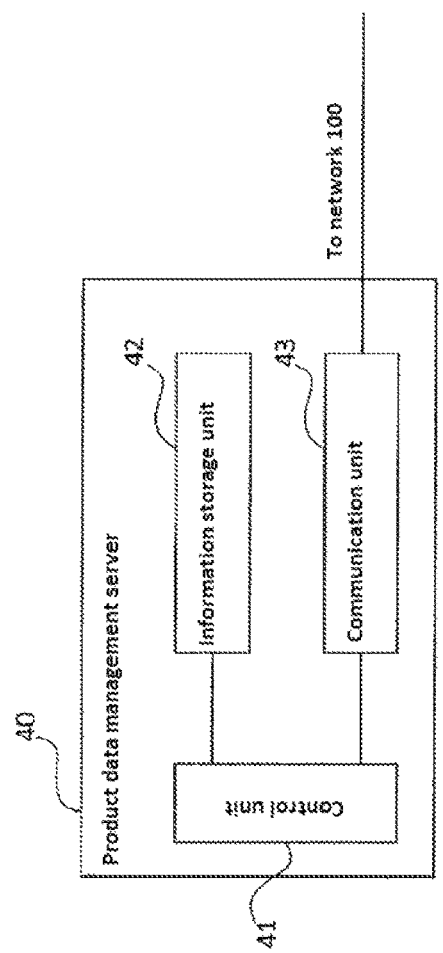
FIG. 9 is a diagram showing a configuration of a product data management server 40.

FIG. 9 is a diagram showing the configuration of the product data management server 40.

As illustrated, the product data management server 40 is comprised of a control unit 41 for controlling the entire product data management server 40, an information storage unit 42 for storing product data, and a communication unit 43 for transmitting/receiving various pieces of information to/from the measuring terminal 20.

Each of the units 41 to 43 is connected to an internal bus. Various pieces of information and the like are inputted and outputted via such a bus. Various processes are executed under the control of the control unit 41.

The control unit 41 is a processing unit responsible for controlling the entire product data management server 40, composed of an electric circuit such as a CPU (Central Processing Unit) or an integrated circuit such an FPGA (Field-Programmable Gate Array).

The control unit 41 executes readout of information from the information storage unit 42 as well as write-in of information into the information storage unit 42.

The information storage unit 42 is a device for storing information, such as a hard disk, memory, or a semiconductor element.

The information storage unit 42 has a region for storing a program executed by the control unit 41, a working region (RAM or the like) that is temporarily used when the control unit 41 executes a process, or the like.

The control unit 41 reads out a program stored in the information storage unit 42 and deploys the program in the working region to execute various processes.

The communication unit 43 is an interface for controlling communication with the measuring terminal 20 via the network 100, having a LAN adapter or the like.

The communication unit 43 can comprise a wireless transceiver and be connected to LAN, Internet, or the like via wireless communication, or can be connected via a wire such as a cable.

Figure 10:
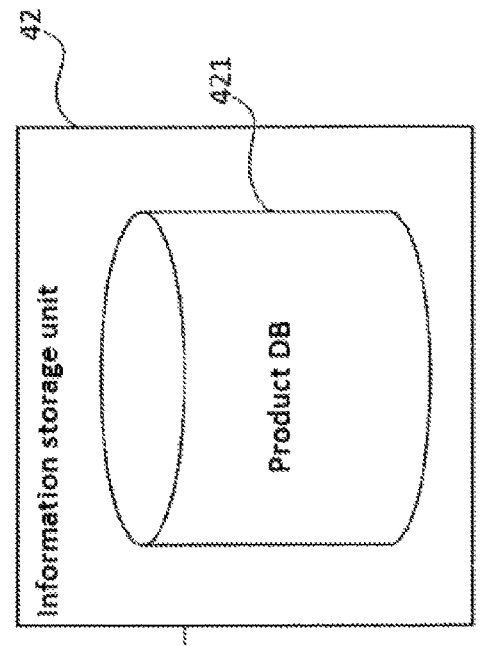
FIG. 10 is a diagram showing data or the like stored by an information storage unit 42 of the product data management server 40.

FIG. 10 is a diagram showing data or the like stored by the information storage unit 42 of the product data management server 40.

As illustrated, the information storage unit 42 stores a product DB 421 for managing product data.

FIG. 11 is a diagram showing an example of a data configuration of a product DB.

As illustrated, the product DB 421 manages product brands supplying footwear, categories of the products, size information for each product, colors of the products, prices of the products, and number of products in stock while associating the data with an ID (product ID) for identifying the product.

Examples of products categories include leather shoes, sneakers, pumps, sandals, boots, and the like. The product categories can be designed to have multiple levels, such as broad category→narrow category. A broad category of "sneakers" can include narrow categories "high cut" and "low cut", so that a product category is designed to be subdivided into narrower categories.

The size information is denoted in common size denotations such as 23.5 cm to 28.5 cm for men's sizes and 21.0 cm to 26.0 cm for women's sizes, or can be denoted in smaller or larger sizes.

The size information can also include denotation that indicates the width or instep height of the footwear.

<Manufacture of Size Measuring Apparatus>

FIG. 12 is a flowchart showing the flow of the manufacture of a size measuring apparatus.

First, a service provider operates the provider terminal 30 to set the placement positions of the markers 12 to any position on the main body of the size measuring apparatus 10 on the display unit 34 (step S101).

For example, when the operation unit 35 is comprised of a mouse or the like, a given sheet-like position on the main body of the size measuring apparatus 10 displayed on the display unit 34 is clicked to set the placement positions of the markers 12.

As described above, the markers 12 are identifiable from one another from the shape, pattern, or the like, and have a preset marker ID, which is an identification number.

To set the placement positions of the markers 12, the service provider selects the marker ID of the marker 12 to be set and sets the placement position of the marker 12.

Once the placement positions of the markers 12 are set, the control unit 31 generates measuring apparatus data indicating the markers 12 placed and set on the surface of the main body of the size measuring apparatus 10, and coordinates indicating the placement positions and identification numbers of the markers 12 (step S102).

In the measuring apparatus data, the coordinates of the placement positions of the markers 12 and identification numbers of the markers 12 are associated with each other, thus indicating which marker 12 is placed on which position of the main body of the size measuring apparatus 10.

When the placement positions of the markers 12 are set, a key marker for determining which direction an image was captured when capturing from a plurality of directions is also set (step S103).

When mounting a foot on the size measuring apparatus 10 and capturing the foot from a plurality of directions, a key marker is set at a position from which the capture direction, e.g., front of foot, right side, or left side, can be recognized. The key marker setting information is also included in the measuring apparatus data described above.

The placement positions of the markers 12 contained in measuring apparatus data are set at positions that do not overlap with the mounting section 11 for mounting a foot by a user.

Next, a device (not shown) for manufacturing the size measuring apparatus 10 manufactures the size measuring apparatus 10 using measuring apparatus data (step S104).

While the manufacturing method of the size measuring apparatus 10 is not particularly limited, if a device for manufacturing the size measuring apparatus 10 is for example an information processing device comprising a printing function or the like, a size measuring apparatus is manufactured upon input of the measuring apparatus data by printing the mounting section 11 and the markers 12 on paper or cloth with a predetermined size, based on the measuring apparatus data.

<Method of Measuring the Foot Size of a User>

Figure 14:
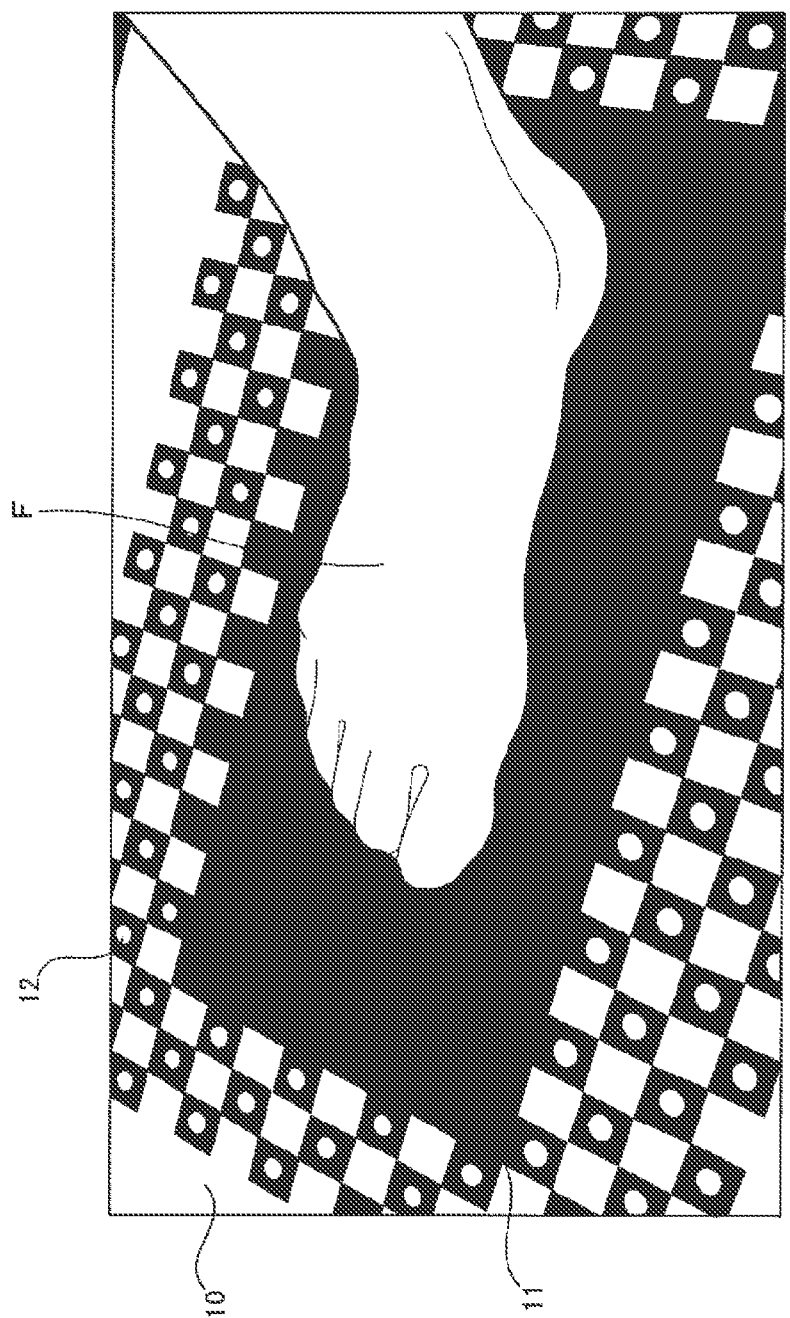
FIG. 14 is a diagram showing a foot being mounted by a user on a mounting section of a size measuring apparatus.
Figure 15:
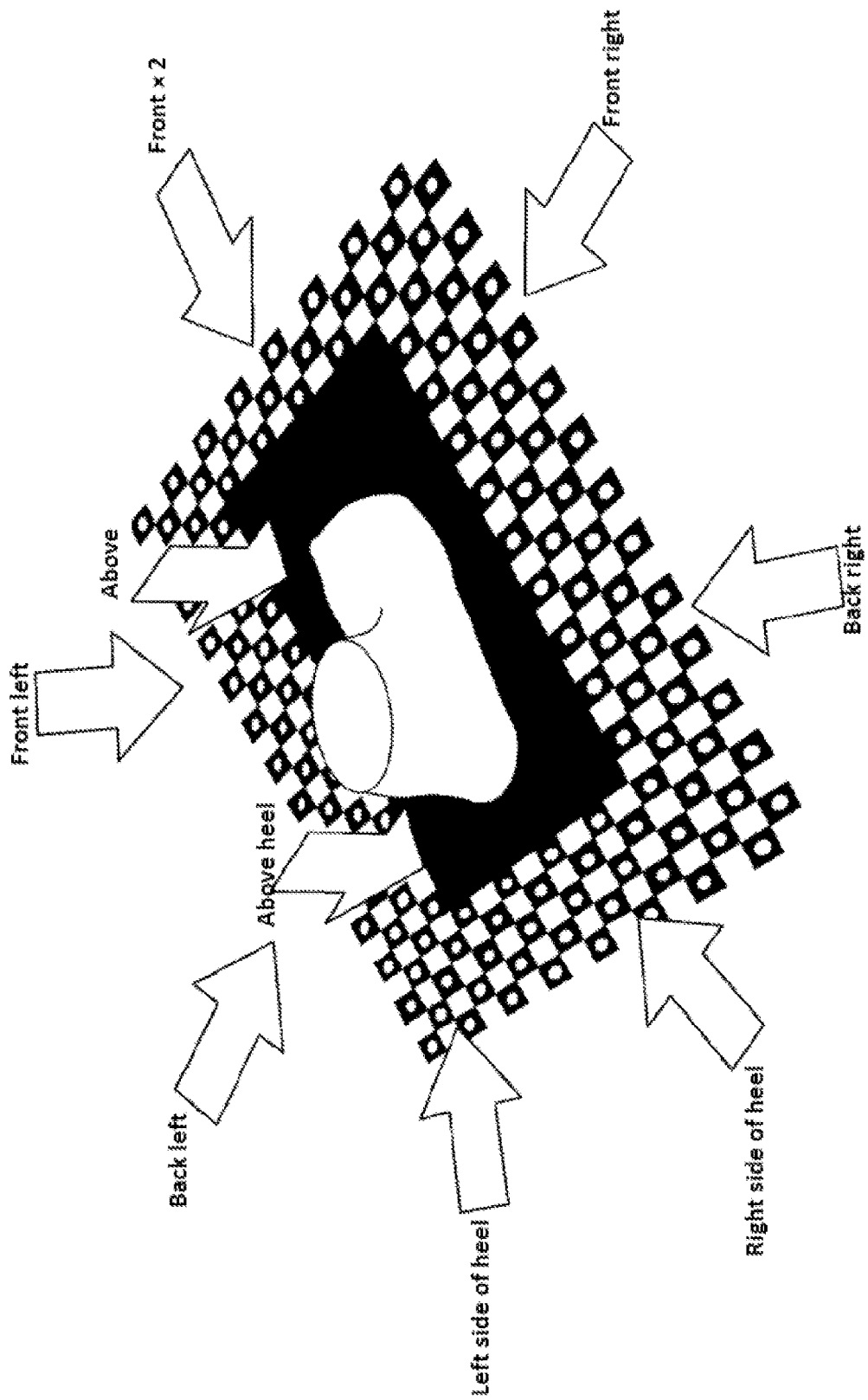
FIG. 15 is a diagram showing directions of capture with a measuring terminal.
Figure 16:
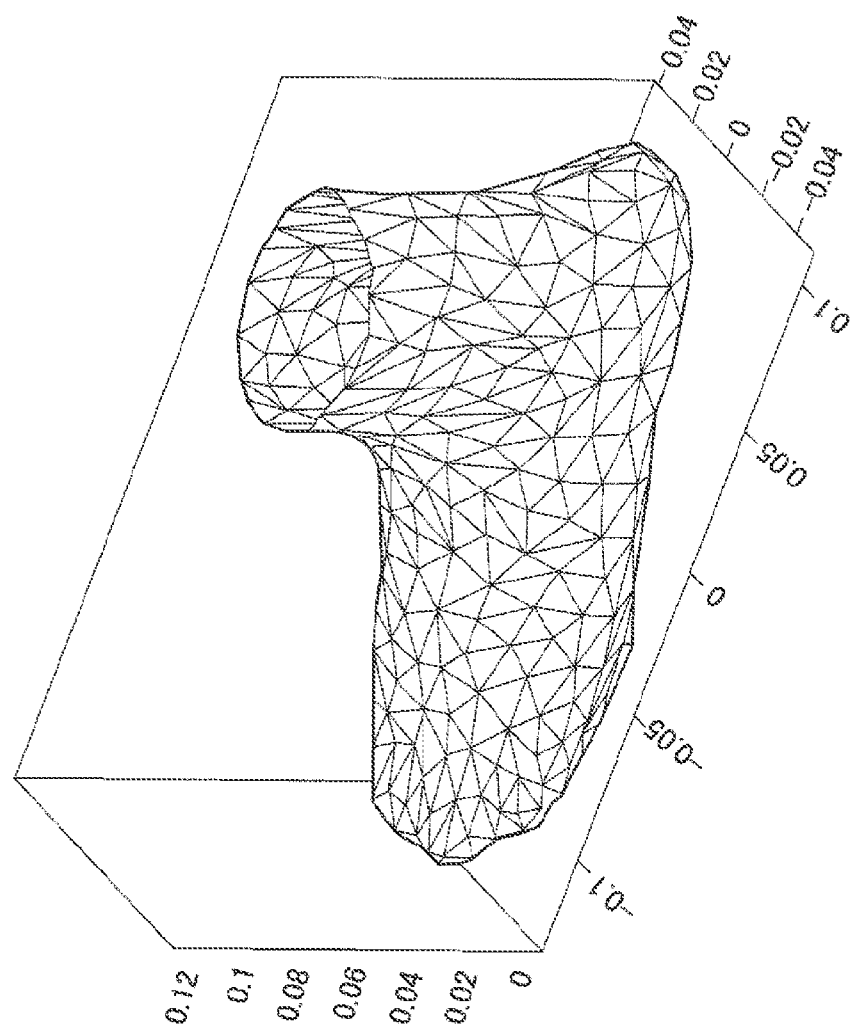
FIG. 16 is a diagram showing an example of a foot model data.
Figure 17:
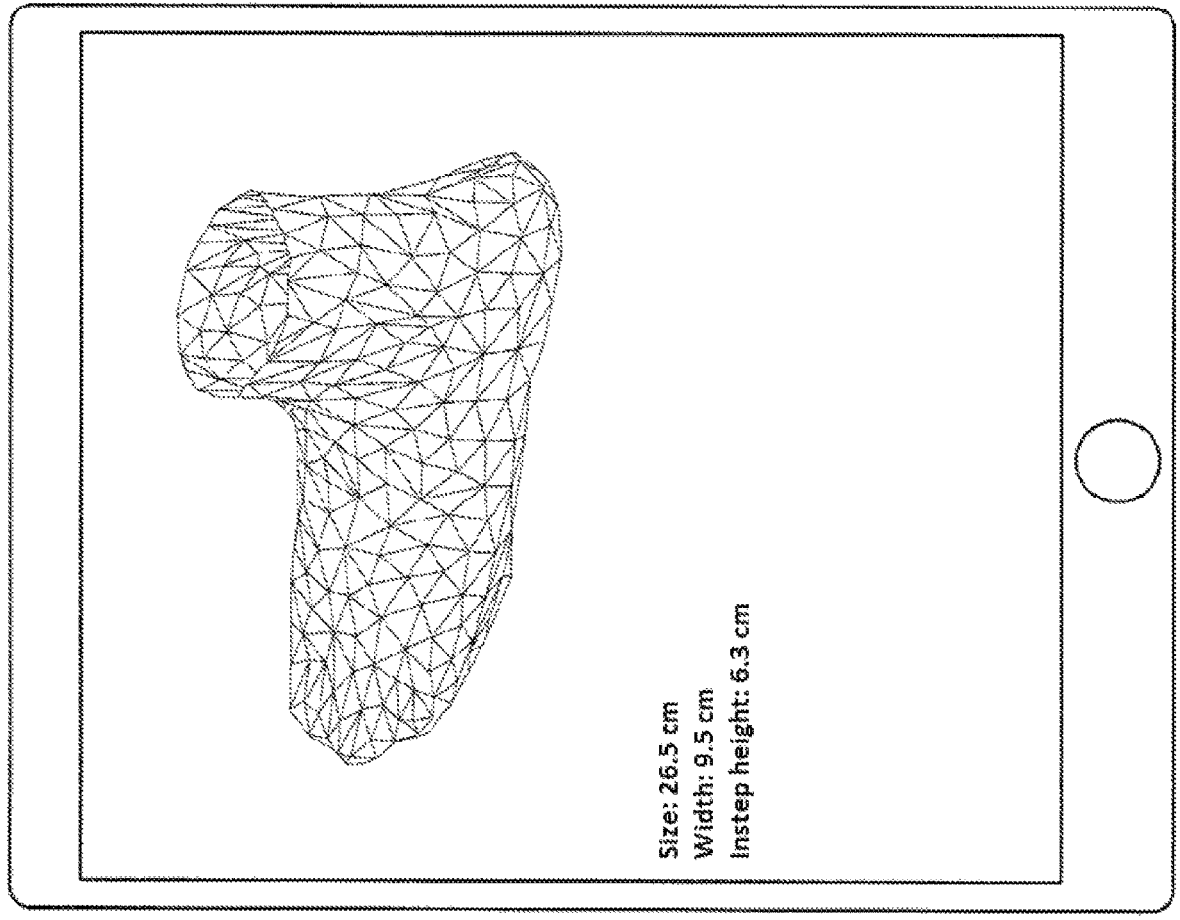
FIG. 17 is a diagram showing an example of results of measurement displayed on a measuring terminal.

FIG. 13A is flowchart showing a method of measuring a foot size of a user. FIG. 14 is a diagram showing a user mounting a foot on a mounting section of a size measuring apparatus. FIG. 15 is a diagram showing directions of capture with a measuring terminal. FIG. 16 is a diagram showing an example of foot model data. FIG. 17 is a diagram showing an example of results of measurement displayed on a measuring terminal.

First, a user mounts the user's own left or right foot F on the mounting section 11 of the size measuring apparatus 10 (step S201). The user's own foot F is mounted on the mounting section 11 of the size measuring apparatus 10 as shown in FIG. 14. The user mounts the foot as close to the center of the mounting section 11 as possible.

Next, the user captures the user's own foot F by using the measuring terminal 10 from a plurality of directions (step S202). As shown in FIG. 15, the user activates the capture unit 26 of the measuring terminal 20, set the mode to the movement capture mode that can capture a video, and capture the user's own foot F from a plurality of directions for several sections each.

For example, the capture direction can be guided by a voice guidance from an application that is preinstalled in the measuring terminal 10 so that the user captures the foot while moving the measuring terminal 10 toward the guided direction in accordance with the voice guidance.

The capture directions are, for example, the following 10 directions.
1. above
2. front
3. front right
4. back right
5. right side of heel
6. front
7. front left
8. back left
9. left side of heel
10. above heel In another example, the capture directions are, for example, the following 7 directions.
1. above
2. front
3. front diagonal right
4. back diagonal right
5. back
6. back diagonal left
7. front diagonal left The aforementioned examples of capture directions are just examples. An image or video can be captured from any direction, in addition to or instead of the directions described above. In a preferred embodiment, capture directions comprises at least directly above. An image from directly above can capture the contour of the entire foot. Thus, precision is improved from generating a 3D model by using an image from direction above. Since an image from directly above can simultaneously capture the whole markers 12 and the foot on the size measuring apparatus, an image from directly above can be used to determine whether a user has mounted a foot in the correct direction with respect to the size measuring apparatus, and/or whether the foot targeted for measurement, between the left and right feet, is mounted. For example, it is possible to determine whether the contour of a foot captured by an image from direction above is significantly different from the expected contour of the foot. If significantly different, processing can be ended as an error because it is highly likely that the user has mounted the foot in the wrong direction with respect to the measuring apparatus, or a foot that is not targeted for measurement between the left and right feet is mounted, or an object other than a foot is mounted.

A user can capture a video for several seconds so that the foot F and the plurality of markers 12 are captured together from each direction. A user only needs to activate video recording and move the measuring terminal 20, with no need to operate a shutter by the user.

The control unit 21 of the measuring terminal 20 determines whether the marker 12 (hereinafter, key marker) required for determining which direction a captured video is captured from is captured when capturing a video of the foot F of the user and the plurality of markers 12 with the capture unit 26. The control unit 21 of the measuring terminal 20 can, in response to the key marker and the foot F entering the field of view of the capture unit 26, capture an image at the time. For example, when a user is instructed to capture an image or video from a specific direction, this allows the control unit 21 of the measuring apparatus 20 to recognize the key marker and the foot F that should be in the field of view of the capture unit 26 and automatically capture and image by simply orienting the capture unit 26 towards the size measuring apparatus 10 and the foot F from a specific direction by the user.

The control unit 21 determines whether a key marker determined for each capture direction is captured by referring to the marker DB 221 stored in the information storage unit 22.

If it is determined that the plurality of markers 12 including the key marker and the foot F have been captured, capturing from this direction is ended. After notifying the user that capturing from said direction has been completed, the user is guided to capture from the next direction.

When video capture from the 10 direction described above by the user is completed, the control unit 21 of the measuring terminal 20 selects the optimally captured frame data from capture data capturing a video from each direction (step S203).

The capture unit 26 has a function that can capture a video at any frame rate such as 10 fps, 10 fps, 30 fps, or 60 fps as described above. The control unit 21 selects the optimally captured (e.g., least amount of blur or most focused) frame data from video data capturing a video from each direction.

Next, the control unit 21 computes parameters (distance and pose) of the measuring terminal 20 when captured by the size measuring apparatus 10 from frame data captured from each direction (step S204).

The distance to the measuring terminal 20 and the pose can be computed by focusing on the plurality of markers 12 captured in each frame data and utilizing triangulation from the distance between each of the markers 12 that can be discerned.

Next, the captured partial contour of the foot is extracted from each frame data (step S205).

The control unit 21 can extract the partial contour of a foot captured in frame data by recognizing the boundary between the mounting section 11 and the partial contour of the foot from each frame data. Such an extraction method can be readily performed by using conventional techniques. For example, the method can be performed by processing such as region growing based on the color of the mounting section 11 and the color of the foot F.

Partial foot contour data for each direction can be obtained by performing such processing for each frame data (e.g., each of 10 directions).

Next, the partial contours of the foot are integrated (step S206).

The control unit 21 generates the contour data for the entire foot by integrating the obtained partial foot contour data for each of 10 directions. The control unit 21 can generate the contour data for the entire foot using, for example, space carving, by using the partial contour data for each direction and the parameters of the measuring terminal 20 upon capture in the same direction.

Next, the control unit 21 generates a foot model (step S207).

For example, the control unit 21 can synthesize the generated contour data for the entire foot with foot model data that approximates the contour data to generate the optimal foot model. The control unit 21 can generate the optimal foot model by obtaining foot model data (see FIG. 16) that approximates the generated contour data for the entire foot from a foot model DB stored in the information storage unit 22 of the measuring terminal 20 and synthesizing the contour data with the approximate foot model data.

In another example, the control unit 21 can generate a foot model based on the generated contour data for the entire foot and the contour data of the default 3D model.

FIG. 13B is flowchart showing an example of processing for measuring the foot size of a user in another example of a method of measuring the foot size of the user described above. This processing is executed in the control unit 21 of the measuring terminal 20.

Before step S301, the same operations as step S201 to step S202 are performed. With such operations, a plurality of images capturing a foot mounted on the size measuring apparatus 10 from a plurality of directions can be obtained. The plurality of obtained images are inputted into the control unit 21 from the capture unit 26.

Once the plurality of images are inputted into the control unit 21, the control unit 21 receives the images of the user (step S301).

Once the images of the user are received, the 3D model constructing means 211 of the control unit 21 constructs a 3D model by modifying the shape of a default 3D model based on the received images (step S302). For example, the control unit 21 can generate contour data for the entire foot by the same processing as steps S203 to step S206 described above and construct a 3D model by using the generated contour data for the entire foot. The 3D model constructing means 211 constructs a 3D model of a user by, for example, modifying the shape of the default 3D model based on the contour of a default 3D model within a virtual image obtained from the default 3D model and the contour of a three-dimensional object within received images. For example, the 3D model constructing means 211 can construct a 3D model by processing 400 described below. The 3D model constructing means 211 can modify the shape of a default 3D model within a virtual three-dimensional space, which is a space generated from expanding or contracting an actual three-dimensional space at a predetermined scale.

When a 3D model is constructed, the measuring means 212 of the control unit 21 measures the foot size in the constructed 3D model (step S303). The measuring means 212 measures the foot size in a virtual three-dimensional space. The measuring means 212 can measure the foot size of a 3D model using a known methodology.

Once the foot size is measured, the converting means 213 of the control unit 21 converts the measured foot size into the actual foot size (step S304). For example, the converting means 213 converts the foot size in a virtual three-dimensional space into a foot size in an actual three-dimensional space using a scale between the virtual three-dimensional space and the actual three-dimensional space. If, for example, the scale between the virtual three-dimensional space and actual three-dimensional space is X:Y, and the foot size in the virtual three-dimensional space measured by the measuring means 212 is measured to be h, the foot size h in the virtual three-dimensional space is converted into the foot size in the actual three-dimensional space by multiplying by Y/X (h×Y/X).

When converted into an actual foot size, the processing 300 for measuring the foot size is complete. The control unit 21 then computes the measurement size data representing the size of a given foot part of a user based on the actual body size.

Figure 13C:
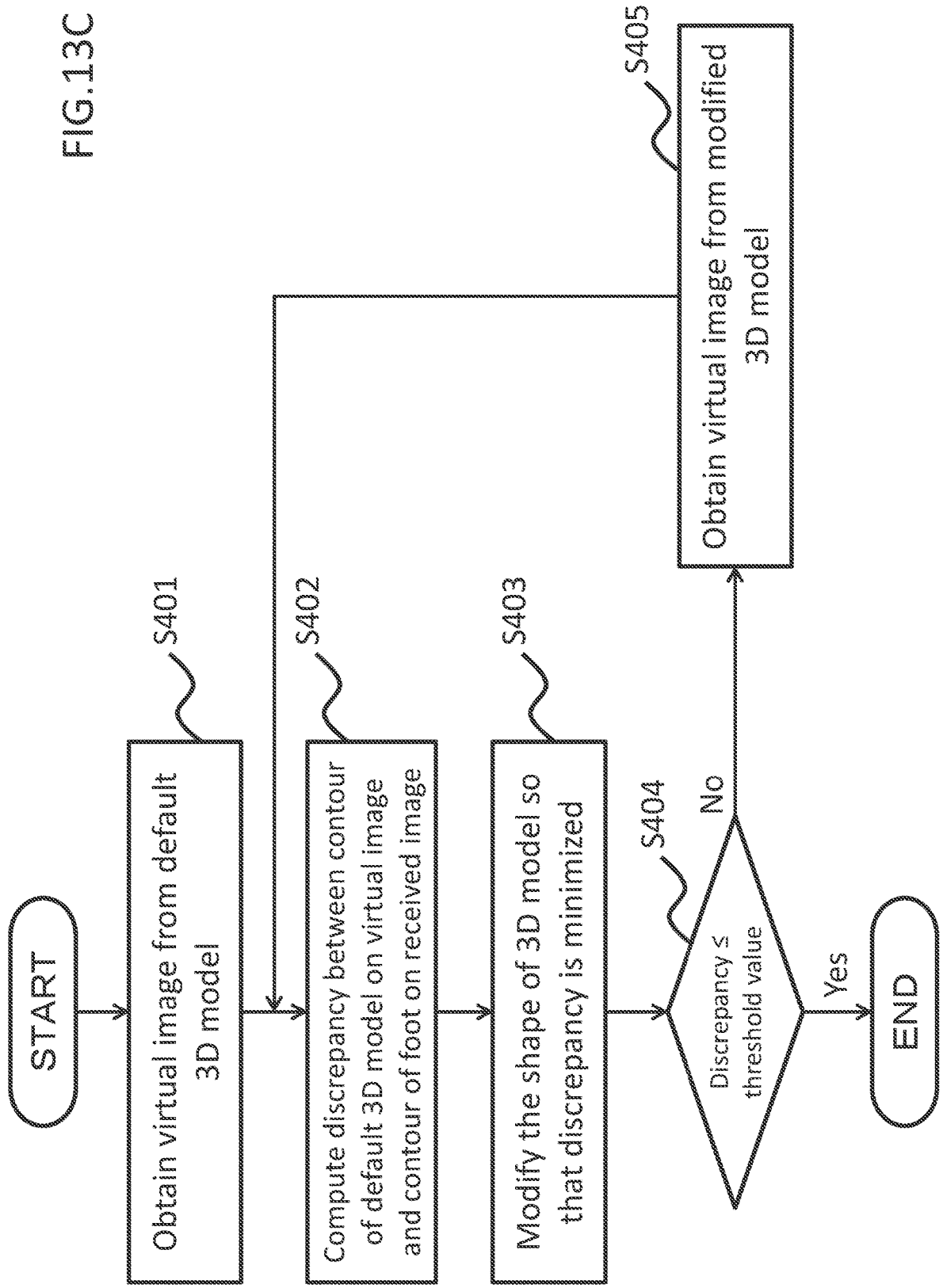
FIG. 13C is a flowchart showing an example of processing for 3D model constructing means 211 to construct a 3D model in step S302.

FIG. 13C is a flowchart showing an example of processing for the 3D model constructing means 211 to construct a 3D model in step S302.

The 3D model constructing means 211 obtains a virtual image from a default 3D model (step S401). A virtual image is an image that has virtually captured a default 3D model from a plurality of directions. The direction of capturing a virtual image can be the same direction as the direction of capturing an image by the measuring terminal 20, and the position of capturing a virtual image can be the same position as the position of capturing an image by the measuring terminal 20. This is because this enables comparison of the contour of the default 3D model on the virtual image with the contour of the foot on the received image. The direction of capture and the position of capture by the measuring terminal 20 can be computed, for example, by using the principle of triangulation based on planar coordinates in a planar space of each of the markers 12 recognized within frame data.

The 3D model constructing means 211 then computes the discrepancy between contour of the default 3D model on the virtual image and the contour of the there-dimensional object on the received image (step S402). For example, the 3D model constructing means 211 can compute the discrepancy between each of the plurality of vertices constituting a default 3D model and possibly corresponding vertices of the three-dimensional objective within the received image. For example, the 3D model constructing means 211 can compute the discrepancy between each of the plurality of curved lines constituting a default 3D model and possibly corresponding curved lines of the three-dimensional objective within the received image. The discrepancy between a marker within the virtual image and a corresponding marker within the received image can be computed, for example, at a pixel level.

The 3D model constructing means 211 then modifies the shape of a default 3D model such that the discrepancy computed in step S403 is minimized (step S403). The 3D model constructing means 121 can derive a modification that minimizes the discrepancy by using, for example, the least square method.

The 3D model constructing means 211 then determines whether the discrepancy is less than or equal to a predetermined threshold value (step S404). If the discrepancy is less than or equal to a predetermined threshold value, the 3D model after the modification is determined as a 3D model of a user. This completes the processing. If the discrepancy is greater than the predetermined threshold value, the process proceeds to step S405. In this regard, the predetermined threshold value can be, for example, 0, or any non-zero value.

If the discrepancy ERR is greater than the predetermined threshold value, the 3D model constructing means 211 obtains a virtual image from the modified 3D model (step S405). The virtual image is an image that has virtually captured the modified 3D model from a plurality of directions. A virtual image obtained from a modified 3D model can be captured from the same direction and same position as the received image in the same manner as a virtual image obtained from a default 3D model.

The 3D model constructing means 211 then repeats step S402 to step S404 using a virtual image obtained from the modified 3D model and the modified 3D model. This is repeated until the discrepancy is less than or equal to the predetermined threshold value.

A 3D model of a user is constructed in this manner.

The aforementioned example describes that step S402 to step S405 are repeated until the discrepancy is less than or equal to the predetermined threshold value, but the present invention is not limited thereto. For example, step S402 to step S405 can be repeated only a predetermined number of times, or step S402 to step S405 can be repeated until the discrepancy is less than or equal to the predetermined threshold value or a predetermined number of repeats is reached.

The control unit 21 displays the generated foot model on the display unit 24 of the measuring terminal 20 (see FIG. 17). The display unit 24 displays a foot model and measurement results (size/width/instep height, or the like). A user can rotate or expand/contract the foot model in the up/down/left/right directions on the display unit 24 by operating the operation unit 25 while looking at the foot model displayed on the display unit 24.

In another embodiment, the shape of the bottom of the foot F of a user or the distribution of body weight applied on the foot F can be measured by providing an elastic article of an elastic material such as rubber or resin, which is elastically deformable especially in the direction of thickness, and the pressure sensor 11a connected to the elastic article to the mounting section 11 of the size measuring apparatus 10, so that analysis to find whether the shape of the bottom of the foot F of the user is "normal", "flat feet", or "high arch" can be performed.

A more accurate foot model can be generated by adding the results of measurement by the pressure sensor 11a to the generation of a foot model described above.

Measurement of pressure by the pressure sensor 11a and the video capturing by the measurement terminal 20 described above can be performed simultaneously. For the pressure sensor 11a and measurement methods of pressure, conventional methodologies can be used, which are not particularly limited.

Pressure can be measured while the foot F of a user is mounted and still on the pressure sensor 11a provided on the mounting section 11, or the pressure can be measured dynamically while walking on the mounting section 11.

In such an embodiment, first, the measuring terminal 20 that is ready to capture a video is placed at a position away from the size measurement apparatus 10. A user then walks so that the foot F would be on the mounting section 11 of the size measuring apparatus 10. The measuring terminal 20 can capture a video of the foot F of the user that is on the mounting section 11.

This enables measurement of the weight distribution as to which part of the foot F bears the heaviest load, as well as measurement of the degree of curvature of the toe during ambulation by capturing a video with the measuring terminal 20.

The shape of the bottom of the foot F and the weight distribution measured in this manner can also be displayed on the display unit 24 of the measuring terminal 20.

As described above, the size measuring system in the embodiment of the invention involves a user mounting the user's own foot F on the mounting section 11 of the size measuring apparatus 10 and the user capturing a video so that the plurality of markers 12 displayed on the size measuring apparatus 10 are captured from a plurality of directions. The measuring terminal 20 can generate a foot model of a user based on a contour image of the foot F captured from a plurality of directions.

Users can readily find their own foot size (length, width, instep height, or the like) from such a foot model. Once a foot model is received from the measuring terminal 20 as data, the product data management server 40 references a product DB, extracts product data on footwear that matches or is within a predetermined range of the foot model, generates screen information showing data on the product, and transmits the information to the measuring terminal 20. Thus, users can readily find footwear that matches the sizes of their own foot F.

According to this embodiment, the size measuring apparatus 10 can be manufactured by printing the mounting section 11 and the markers 12 on a material such as paper or cloth, which can be processed into a sheet-like form or mat-like form that can be mounted on the floor or the like. Thus, the size measuring apparatus can be mass produced at a low cost.

The pressure sensor 11a can be further provided to the mounting section 11 of the size measuring unit 10. The shape of the bottom of the foot F or the weight distribution can be measured by a user mounting their own foot F on the mounting section 11. In addition, a video of the foot F can be simultaneously captured.

The measuring terminal 20, provider terminal 30, and product data management server 40 are materialized primarily with a CPU and a program loaded into the memory. However, the device or server can be comprised of a combination of any other hardware and software. Those skilled in the art can readily understand the high degree of freedom in the design thereof.

When the measuring terminal 20, provider terminal 30, or product data management server 40 is configured as a software module group, the program can be configured to be recorded on a recording medium such as an optical recording medium, magnetic recording medium, photomagnetic recording medium, or semiconductor and loaded from the recording medium, or loaded from an external equipment connected via a predetermined network.

The aforementioned embodiment is an example of a suitable embodiment of the invention. The embodiment of the invention is not limited thereto. Various modifications can be applied to the extent that the embodiment does not delineate from the spirit of the invention.

This embodiment describes that the subject of measurement is the foot, but the subject is not particularly limited to a foot. The invention can also measure a part of the body such as a hand or head. The subject is not particularly limited, as long as it is a tangible object whose size can be measured. Specifically, the size measuring system of the invention can measure the size of any three-dimensional object. Any three-dimensional object can be, for example, an organism such as an animal or an object that is not an organism. The size measuring system of the invention can be configured to measure the size of the entire three-dimensional object, or the size of a part of a three-dimensional object. The size measuring system of the invention can measure the size of a three-dimensional object from processing that is the same as the processing described above by mounting a portion of a three-dimensional object whose size is to be measured (i.e., entire three-dimensional object or a part thereof) on the size measuring apparatuses 10 and 10' of the invention and capturing the image thereof.

REFERENCE SIGNS LIST

10 Size measuring apparatus
11 Mounting section
11a Pressure sensor
12 Markers
13, 23, 43 Communication unit
20 Measuring terminal
21, 31, 41 Control unit
22, 32, 42 Information storage unit
24, 34 Display unit
25, 35 Operation unit
26 Capture unit
221 Marker DB
222 Foot model DB
30 Provider terminal
321 Foot model data
322 Marker data
40 Product data management server

The invention claimed is:

1. A computer system for measuring a size of a three-dimensional object, the computer system comprising:
   a processor configured to:
   receive an image of a three-dimensional object, the image being an image capturing the three-dimensional object mounted on a size measuring apparatus having a plurality of markers, the plurality of markers comprising a unique marker within the size measuring apparatus; and
   construct a 3D model of the three-dimensional object by modifying a shape of a default 3D model based on the default 3D model and the received image,
   wherein the computer system comprises a camera for capturing the three-dimensional object, wherein the processor is configured to, in the process of taking the image of the three-dimensional object mounted on the size measuring apparatus, identify an orientation direction of the camera based on the plurality of markers and capture the image of the three-dimensional object upon the camera being oriented in an instructed specific direction relative to the three- dimensional object.

2. The computer system of claim 1, wherein the processor constructs the 3D model of the three-dimensional object by modifying the shape of the default 3D model based on a contour of the default 3D model within a virtual image obtained from the default 3D model and a contour of the three-dimensional object within the received image.

3. The computer system of claim 1, the processor is further configured to:
   measure a size in the 3D model; and
   convert the measured size into an actual size;
   wherein the shape of the default 3D model is modified within a virtual three-dimensional space whose scale with respect to an actual three-dimensional space is predetermined, and
   wherein the processor converts the measured size into an actual size by using the scale.

4. The computer system of claim 3, wherein the scale between the virtual three-dimensional space and the actual three-dimensional space is predetermined by a ratio of a size of a plurality of markers of the size measuring apparatus within the virtual three-dimensional space to a size of the plurality of markers of the size measuring apparatus within the actual three-dimensional space.

5. The computer system of claim 1, wherein the specific direction includes directly above the three-dimensional object.

6. The computer system of claim 1, wherein the plurality of markers have an identification element, the identification element being a plurality of dots placed in a unique pattern.

7. The computer system of claim 1, wherein the three-dimensional object is a foot.

8. A size measuring system comprising:
   the computer system of claim 1; and a size measuring apparatus for measuring a size of a three-dimensional object, the size measuring apparatus comprising:
- a mounting section for mounting the three-dimensional object; and
- a plurality of markers placed on the periphery of the mounting section;
- wherein the plurality of markers comprise a unique marker within the size measuring apparatus.

9. The size measuring system of claim 8, wherein the plurality of markers have an identification element, the identification element being a plurality of dots placed in a unique pattern.

10. The size measuring system of claim 8, wherein the size measuring apparatus is formed in a sheet-like form.

11. A non-transitory computer readable medium comprising a program for measuring a size of a three-dimensional object, the program being executed in a computer system having a processor, wherein the program instructs the processor to perform processing comprising:
- receiving an image of a three-dimensional object, the image being an image capturing the three-dimensional object mounted on a size measuring apparatus having a plurality of markers and the plurality of markers comprising a unique marker within the size measuring apparatus; and
- constructing a 3D model of the three-dimensional object by modifying a shape of a default 3D model based on a contour of the three-dimensional object within the received image,
- wherein the computer system comprises a camera for capturing the three-dimensional object, wherein the processor is configured to, in the process of taking the image of the three-dimensional object mounted on the size measuring apparatus, identify an orientation direction of the camera based on the plurality of markers and capture the image of the three-dimensional object upon the camera being oriented in an instructed specific direction relative to the three- dimensional object.

12. A method for measuring a size of a three-dimensional object, comprising:
- capturing an image of a three-dimensional object with a camera, the image being an image capturing the three-dimensional object mounted on a size measuring apparatus having a plurality of markers and the plurality of markers comprising a unique marker within the size measuring apparatus;
- receiving the captured image; and
- constructing a 3D model of the three-dimensional object by modifying a shape of a default 3D model based on a contour of the three-dimensional object within the received image,
- wherein the capturing the image comprises, in the process of taking the image of the three-dimensional object mounted on the size measuring apparatus, identifying an orientation direction of the camera based on the plurality of markers and capturing the image of the three-dimensional object upon the camera being oriented in an instructed specific direction relative to the three- dimensional object.

* * * * *